US007833964B2

(12) United States Patent
Clark

(10) Patent No.: US 7,833,964 B2
(45) Date of Patent: Nov. 16, 2010

(54) METHODS OF REDUCING VISCERAL FAT BY INCREASING LEVELS OF INSULIN-LIKE GROWTH FACTOR-I (IGF-I)

(75) Inventor: Ross G. Clark, Auckland (NZ)

(73) Assignee: Tercica, Inc., Brisbane, CA (US)

( * ) Notice: Subject to any disclaimer, the term of this patent is extended or adjusted under 35 U.S.C. 154(b) by 158 days.

(21) Appl. No.: 10/923,515

(22) Filed: Aug. 20, 2004

(65) Prior Publication Data
US 2005/0043240 A1 Feb. 24, 2005

Related U.S. Application Data

(60) Provisional application No. 60/497,008, filed on Aug. 21, 2003.

(51) Int. Cl.
A61K 38/00 (2006.01)
A61B 5/55 (2006.01)
(52) U.S. Cl. .............................. 514/2; 424/9.3; 530/399
(58) Field of Classification Search ........................ None
See application file for complete search history.

(56) References Cited

U.S. PATENT DOCUMENTS

| 4,988,675 | A | | 1/1991 | Froesch et al. |
| 5,126,324 | A | | 6/1992 | Clark et al. |
| 5,579,782 | A | | 12/1996 | Masuo |
| 5,597,797 | A | * | 1/1997 | Clark ........................... 514/12 |
| 6,643,542 | B1 | * | 11/2003 | Kawanishi ................... 600/547 |
| 6,846,800 | B1 | | 1/2005 | Johannsson et al. |
| 7,122,515 | B2 | | 10/2006 | Johannsson et al. |

FOREIGN PATENT DOCUMENTS

| WO | WO91/18621 A1 | 12/1991 |
| WO | WO94/09813 A1 | 5/1994 |
| WO | WO9738709 A1 | 10/1997 |

OTHER PUBLICATIONS

Woods et al., J. Clin. Endocrin. Metab. 85: 1407-1411, 2000.*
Min et al., Endocrin. 137: 1129-1137, 1996.*
Clemmons et al., J. Clin. Endocr. Metab. 85:1518-1524, 2000.*
Kunitomi et al., Int. J. Obesity 26: 361-369, 2002.*
Moses et al., Diabetes, 45: 91-100, 1996.*
Frayn, Brit. J. Nutrition, 83 (Suppl): S71-77, 2000.*
Hong et al., J. Clin Endocr. Metab. 83: 4239-4245, 1998.*
Gabriely et al., Diabetes, 51: 2951-2958, 2002.*
Johannsson et al., J. Clin. Endocr. Metab. 82: 727-734, 1997.*
Tulloch-Reid et al., Diabetes Care 26: 2556-2561, 2003.*
American Diabetes Association (ADA), Diabetes Care, 22: 99-111, 1996.*
Miller et al., Lancet 351: 871-875,1998.*
Goodpaster et al., Diabetes 48: 839-847, 1999.*
Arnhold et al., "Lack of reduction in body fat after treatment with insulin-like growth factor-I in two children with growth hormone gene deletions", 2000, J Endocrinol Invest 23:258-262.

Bolinder et al., "Studies of acute effects of insulin-like growth factors I and II human fat cells", 1987, Clin Endocrinol Metab, 65:732-737.
Carlsson et al., "Growth hormone and growth in diabetic rats: effects of insulin and insulin-like growth factor-I infusions", 1989, J Endocrin 122:661-670.
Froesch et al., "Therapeutic potential of insulinlike growth factor I", 1990, Trends Endocrinol Metab, 254-260.
Guler et al., "Short-term metabolic effects of recombinant human insulin like growth factor I in healthy adults", 1987, N Engl J Med, 317:137-140.
Giacca et al., "Differential effects of IGF-I and insulin on glucoregulation and fat metabolism in depancreatized dogs", 1990, Diabetes, 39:340-347.
Guevara-Aguirre et al., "Two-year treatment of growth hormone (GH) receptor deficiency with recombinant Insulin-like growth factor I in 22 children: comparison of two dosage levels and to GH-Deficiency", 1997, J Clin Endocrinol Metab 82:629-633.
Grinspoon et al., "Effects of recombinant human insulin-like growth factor (IGR)-I and estrogen administration on IGF-I, IGF binding protein (IGFBP)-2, and IFGBP-3 in anorexia nervosa: a randomized-controlled study", 2003, J Clin Endocrinol Metab 88: 1142-1149.
Isozaki O., "Interaction between leptin and growth hormone (GH) IGF-I axis", Endocr J Mar. 1999;46 Suppl:S17-24.
Koutkia P., "Growth hormone-releasing hormone in HIV-infected men with lipodystrophy: a randomized trial". JAMA Jul. 14, 2004;292(2):210-8.
Kunitomi M., "Relationship between reduced serum IGF-I levels and accumulation of visceral fat in Japanese men", Int J Obes Relat Metab Disord. Mar. 2002;26(3):361-9.
Laron et al., "IGF-I treatment of adult patients with laron syndrome: preliminary results", 1994, Clin Endocrinol 41:631-638.
Mauras et al., "Recombinant human insulin-like growth factor I has signification anabolic effects in adults with growth hormone receptor deficiency: studies on protein, glucose, and lipid metabolism", 2000, J Clin Endcrinol Metab 85:3036-3042.
Svensson J. et al. "Effects of GH and insulin-like growth factor I on body composition", J Endocrinol Invest Sep. 2003;26(9):823-31.
Zenobi et al., "Effects of insulin-like growth factor-I on glucose tolerance insulin levels, and insulin secretion", 1992, J Clin Invest, 89:1908-1913.

(Continued)

*Primary Examiner*—Robert Landsman
*Assistant Examiner*—Gyan Chandra
(74) *Attorney, Agent, or Firm*—Paula A. Borden; Bozicevic, Field & Francis LLP

(57) ABSTRACT

The present invention provides methods and compositions for reducing visceral fat by administering to the subject a therapeutically effective amount of a compound that increases the bioactive serum levels of insulin-like growth factor-I (IGF-I) in the subject, thereby ameliorating negative effects of visceral obesity. The invention is useful in the treatment, prevention, or amelioration of one or more symptoms of visceral obesity or IGF-I deficiency related condition, including, for example, cardiovascular disease and the metabolic syndrome.

22 Claims, 1 Drawing Sheet

OTHER PUBLICATIONS

Zapf et al., "Acute metabolic effects and half-lives of intravenously administered insulinlike growth factors I and II in normal and Hypophysectomized Rats",1986, J Clin Invest, 77:1768-1755.

Zapf et al., "Insulin-like growth factors I and II: Some biological actions and receptor binding characteristics of two purified constituents of nonsuppressible insulin-like activity of human serum", 1978, Eur J Biochem, 87:285-296.

Maccario et al. Effects of 36 hours fasting on GH/IGF-I axis and metabolic parameters in patients with simple obesity. Comparison with normal subjects and hypopituitary patients with severe GH deficiency. (2001) Int. J. Obesity 25:1233-1239.

Schoen et al. Lack of association between adipose tissue distribution and IGF-1 and IGFBP-3 in men and women. (2002) Cancer Epidemiology, Biomarkers and Prevention 11:581-586.

Nam et al. Effect of obesity on total and free insulin-like growth factor (IGF)-1, and their relationship to IGF-binding protein (BP)-1, IGFBP-2, IGFBP-3, insulin, and growth hormone. (1997) Int'l J. Obesity 21:355-359.

Nam, et al. Low-dose growth hormone treatment combined with diet restriction decreases insulin resistance by reducing visceral fat and increasing muscle mass in obese type 2 diabetic patients. Int J Obes Relat Metab Disord. Aug. 2001;25(8):1101-7.

Zvi Laron. Somatomedin-1 (recombinant insulin-like growth factor-1): clinical pharmacology and potential treatment of endocrine and metabolic disorders. BioDrugs. Jan. 1999;11(1):55-70.

Ross Clark. Recombinant human insulin-like growth factor I (IGF-I): risks and benefits of normalizing blood IGF-I concentrations. Horm Res. 2004;62 Suppl 1:93-100.

Johannsson et al. Growth hormone treatment of abdominally obese men reduces abdominal fat mass, improves glucose and lipoprotein metabolism, and reduces diastolic blood pressure. Journal of Clinical Endocrinology and Metabolism, 1997, vol. 82, No. 3, pp. 727-734.

Johannsson et al. Two years of growth hormone (GH) treatment increase isometric and isokinetic muscle strength in GH-deficient adults. Journal of Clinical Endocrinology and Metabolism, 1997, vol. 82, No. 9, pp. 2877-2884.

Johannsson et al. Growth hormone-deficient adults are insulin-resistant. Metabolism, 1995, vol. 44, No. 9, pp. 1126-1129.

Grundy, et al. Definition of metabolic syndrome- report of the national heart, lung, and blood institute/american heart association conference on scientific Issues related to definition. Circulation, Journal of the American heart association, 2004, vol. 109, pp. 433-439.

The IDF: Consensus worldwide definition of the metabolic syndrome. IDF promoting diabetes care, prevention and a cure worldwide. 2006, pp. 1-16.

Bjorntorp. Visceral obesity: a "civilization syndrome." Obesity research. 1993, vo. 1, No. 4, pp. 206-222.

Reaven. Role of insulin resistance in human disease. Diabetes, 1988, vol. 37, pp. 1595-1607.

Fowelin, et al. Effects of treatment with recombinant human growth hormone on insulin sensitivity and glucose metabolism and adults with growth hormone deficiency. Metabolism, 1993, vol. 42, No. 11, pp. 1443-1447.

Richelsen, et al. Growth hormone treatment of obese woman for 5 wk: effect on body composition and adipose tissue LPL activity. Growth Hormone Effect on Body Composition in Obesity. 1994, pp. E211-E216.

Taaffe, et al. Recombinant human growth hormone, but not insulin-like growth factor-I, enhances central fat loss in postmenopausal women undergoing a diet and exercise program. Horm Metab Res, 2001, vol. 33, 156-162.

Thompson, et al. Effects of human growth hormone, insulin-like growth factor I, and diet and exercise on body composition of obese postmenopausal women. Journal of Clinical Endocrinology and Metabolism, 1998, vol. 83, No. 5, pp. 1477.

* cited by examiner

METHODS OF REDUCING VISCERAL FAT BY INCREASING LEVELS OF INSULIN-LIKE GROWTH FACTOR-I (IGF-I)

CROSS-REFERENCE TO RELATED APPLICATION

This application claims the benefit of U.S. Provisional Application No. 60/497,008, filed Aug. 21, 2003, which application is incorporated herein by reference.

FIELD OF THE INVENTION

The invention relates to methods and compositions for reducing visceral fat in a subject.

BACKGROUND OF THE INVENTION

Obesity is associated with a decreased life span and many medical conditions including metabolic problems of insulin resistance, and diabetes mellitus and its many sequelae, including renal disease, eye disease, and cardiovascular disease. See Rissanen et al., 1990, Br Med J, 301:835-837.

Obesity is a risk factor for many conditions, particularly diabetes, more particularly Type II diabetes. Omental and mesenteric adipose depots, representing so-called visceral adiposity, are the fat depots most strongly associated with obesity-induced insulin resistance, especially in skeletal muscle and liver, so that a high level of visceral adipose tissue is associated with reduced glucose tolerance (Despres J P, 1993, Nutrition 9:452-459; Kissebah A H et al., 1994, Physiol Rev 74:761-811). For example, in men and in women the accumulation of intra-abdominal or visceral fat correlates with insulin resistance, whereas the deposition of subcutaneous fat only correlates with circulating leptin levels, rather than with insulin resistance (M Cnop et al., 2002, Diabetes, 51:1005-1015). Most significantly, the relationship between visceral fat deposition and glucose tolerance remains significant after correcting for the level of total-body fat. In other words, it is not only the amount of body fat that is important, the distribution or location of the body fat in the body is also important with the amount visceral fat being of greatest importance.

IGF-I admininstration in human subjects has had little effect on body fat and body composition. See Guevara-Aguirre et al., 1997, J Clin Endocrinol Metab 82:629-633, Mauras et al., 2000, J Clin Endcrinol Metab 85:3036-3042 and Laron et al., 1994, Clin Endocrinol 41:631-638 (Laron's Syndrome); Arnhold et al., 2000, J Endocrinol Invest 23:258-262 (short stature in children lacking Growth Hormone gene); Grinspoon et al., 2003, J Clin Endocrinol Metab 88: 1142-1149 (anorexia nervosa); and U.S. Pat. No. 5,597,797. In these studies the effect of IGF-I on body fat distribution or visceral fat was not assessed.

In Japanese men, reduced IGF-I levels were associated with increased visceral fat and the fall in visceral fat associated with exercise was positively correlated with an exercise-induced increase in IGF-I levels. See Kunitomi M et al., 2002, Int J Obes Relat Metab Disord 26:361-369. However, the effect of administration of IGF-I on body fat in mammals has produced conflicting results. Recombinant human IGF-I injected in castrated male sheep lowered insulin levels, but had no detectable effect on body fat. See Certain et al., 1992, Endocrinol 130:2924-2930. This is consistent with their earlier work in mice. See Siddiqui et al., 1990, J Endocrinol, 124:151-158. In another study, IGF-I administered to rats, in which a catabolic state was induced by diabetes, dexamethasone, or intestinal resection, resulted in a trend toward a lower percentage of body fat. See Ballard et al. in Modern Concepts of Insulin-like Growth Factors, ed. Spencer, p. 617-627 (1991). In mini-poodles treated with recombinant human IGF-I, there was a reduced body mass index. See Guler et al., 1990, Acta Endo 121:456-464. Notably, in all of these studies, the effect on body fat distribution or visceral fat was not examined.

Existing therapies for obesity include standard diets and exercise, very low calorie diets, behavioral therapy, pharmacotherapy involving appetite suppressants, thermogenic drugs, food absorption inhibitors, mechanical devices such as jaw wiring, waist cords and balloons, and surgery. See Jung and Chong, 1991, Clinical Endocrinology, 35:11-20; Bray, 1992, Am J Clin Nutr 55:538S-544S. Protein-sparing modified fasting has been reported to be effective in weight reduction in adolescents. See Lee et al., 1992, Clin Pediatr, 31:234-236. Caloric restriction as a treatment for obesity causes catabolism of body protein stores and produces negative nitrogen balance. Protein-supplemented diets, therefore, have gained popularity as a means of lessening nitrogen loss during caloric restriction. Because such diets produce only modest nitrogen sparing, a more effective way to preserve lean body mass and protein stores is needed. In addition, treatment of obesity would be improved if such a regimen also resulted in accelerated loss of body fat. Various approaches to such treatment include those discussed by Weintraub and Bray, 1989, Med Clinics N Amer 73:237; Bray, 1991, Nutr Rev, 49:33.

Thus, there remains a need in the art for methods to reduce visceral fat, as well as to prevent visceral fat deposition, ameliorate visceral fat deposition caused by a medicament, and to provide for reduction of visceral fat as a part of weight loss induction.

The present invention address these needs

LITERATURE

Literature of interest includes: U.S. Pat. No. 4,988,675, U.S. Pat. No. 5,597,797; Froesch et al., 1990, Trends Endocrinol Metab, 254-260; Guler et al., 1987, N Engl J Med, 317:137-140; Carlsson et al., 1989, J Endocrin 122:661-670; Zenobi et al., 1992, J Clin Invest, 89:1908-1913; Zapf et al., 1986, J Clin Invest, 77:1768-1755; Guler et al., 1987, N Engl J Med, 317:137-140; Zapf et al., 1978, Eur J Biochem, 87:285-296; Bolinder et al., 1987, Clin Endocrinol Metab, 65:732-737; Giacca et al., 1990, Diabetes, 39:340-347; Guevara-Aguirre et al., 1997, J Clin Endocrinol Metab 82:629-633, Mauras et al., 2000, J Clin Endcrinol Metab 85:3036-3042 and Laron et al., 1994, Clin Endocrinol 41:631-638; Arnhold et al., 2000, J Endocrinol Invest 23:258-262; Grinspoon et al., 2003, J Clin Endocrinol Metab 88: 1142-1149.

SUMMARY OF THE INVENTION

The present invention provides methods and compositions for reducing visceral fat by administering to the subject a therapeutically effective amount of a compound that increases the bioactive serum levels of insulin-like growth factor-I (IGF-I) in the subject, thereby ameliorating negative effects of visceral obesity. The invention is useful in the treatment, prevention, or amelioration of one or more symptoms of visceral obesity or IGF-I deficiency related condition, including, for example, cardiovascular disease and the metabolic syndrome.

In one aspect the invention features a method for reducing visceral fat in a subject, comprising administering to a subject having visceral fat an amount of a compound that increases the bioactive serum levels of insulin-like growth factor-I (IGF-I) to reduce the visceral fat in said subject, wherein the compound is not growth hormone. In one embodiment the reduction in visceral fat is assessed by determining the ratio of visceral fat to subcutaneous fat. In another embodiment, the reduction in visceral fat is assessed by a decrease in a ratio of waist measurement to hip measurement of the subject. In yet another embodiment, the reduction in visceral fat is assessed by computer tomography (CT) scan.

In one aspect, the viscerally obese subject is also diabetic. In another aspect, the diabetic subject has metabolic syndrome. In another aspect, the invention provides methods for reducing the ratio of visceral fat to subcutaneous fat by administration of a compound that increases serum levels of bioactive IGF-I in a subject that is IGF-I deficient. In one aspect, the IGF-I deficient subject exhibits short stature. In one aspect, the IGF-I deficient subject exhibits short stature and is diabetic. In certain embodiments, the methods of the invention can be used with diabetic subjects in which lower doses of insulin are required to treat the subject compared to treatment of the subject with insulin alone. In another embodiment in lower doses of an oral hypoglycemic agent are required to treat the subject compared to treatment of the subject with the oral hypoglycemic agent alone In some embodiments, the compound that increases the bioactive serum levels of insulin-like growth factor-I (IGF-I) is IGF-I. In further embodiments, the IGF-I is complexed with insulin-like growth factor binding protein-3 (IGFBP-3). In other further embodiments, the amount of IGF-I is in the range of about 10 µg/kg/day to about 80 µg/kg/day, including about 20 µg/kg/day to about 70 µg/kg/day, such as about 30 µg/kg/day to about 60 µg/kg/day. In yet further embodiments, IGF-I is administered subcutaneously. In another embodiment, the compound that increases the bioactive serum levels of insulin-like growth factor-I (IGF-I) is a growth promoting agent that is not growth hormone.

In other embodiments, the compound that increases the bioactive serum levels of IGF-I is an IGF-I displacer. In other embodiments, the compound that increases the bioactive serum levels of IGF-I is a dietary supplement.

In other embodiments, the compound that increases the bioactive serum levels of IGF-I is administered with an effective amount of a hypoglycemic agent which increases insulin levels or improves insulin action. In further embodiments, the hypoglycemic agent to increase insulin levels is insulin. In other further embodiments, the hypoglycemic agent to increase insulin levels or increase insulin sensitivity is selected from the group consisting of sulfonylureas, biguanides and thiazolidinediones. In other further embodiments, the hypoglycemic agent is glyburide.

In other embodiments, the compound that increases the bioactive serum levels of IGF-I is administered with an effective amount of an IGF binding protein. In further embodiments, the IGF binding protein is an insulin-like growth factor binding protein (IGFBP).

Another aspect of the present invention provides a method for preventing visceral fat deposition in a subject, comprising administering to a subject an effective amount of a compound that increases the bioactive serum levels of insulin-like growth factor-I (IGF-I) to prevent visceral fat deposition in the subject. In such embodiments the object is to prevent the accumulation of fat that occurs due to factors such as age, such as that which occurs for example at puberty, or at menopause.

Yet another aspect the present invention provides a method of ameliorating visceral fat deposition caused by a medicament, comprising co-administering to a subject along with a medicament an effective amount of a compound that increases the bioactive serum levels of insulin-like growth factor-I (IGF-I), to ameliorate visceral fat deposition, wherein the compound is not growth hormone. In some embodiments, the object of the invention is to prevent the accumulation of visceral fat that occurs with drug administration, such as that which occurs with compounds which increase insulin levels such as insulin or glyburide, or compounds that increase insulin sensitivity.

In some embodiments, the compound that increases the bioactive serum levels of IGF-I is IGF-I, preferably such as recombinant human IGF-1.

DEFINITIONS

Figure 1:
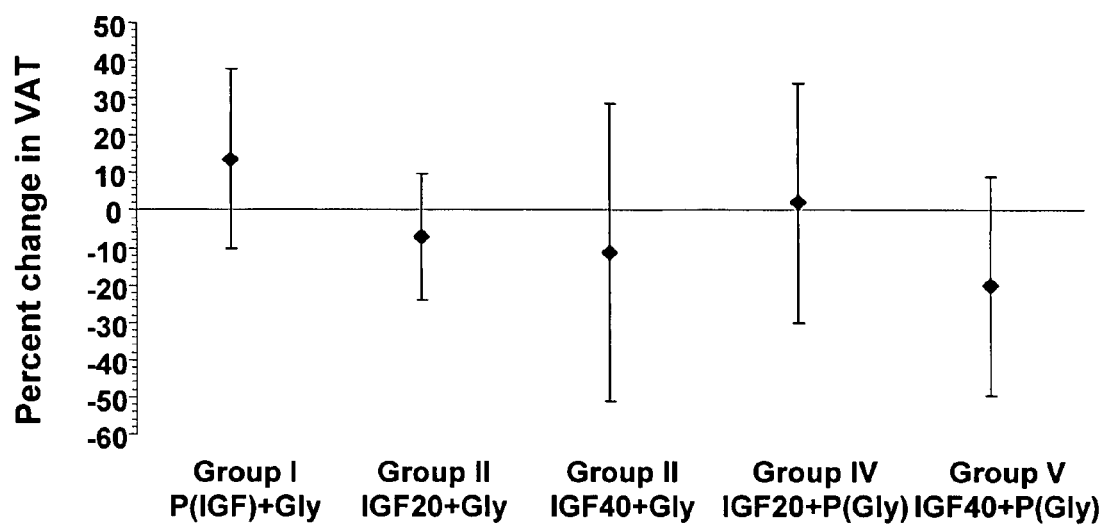
FIG. 1 is graph showing the percent change in visceral fat in response to treatment with either IGF-I alone or in combination with the hypoglycemic agent glyburide. Group One was administered glyburide and a IGF-I placebo. Group Two was administered 20 µg/kg of IGF-I and glyburide. Group Three was administered 40 µg/kg of IGF-I and glyburide. Group Four was administered 20 µg/kg of IGF-I and a glyburide placebo. Group Five was administered 40 µg/kg of IGF-I and a glyburide placebo.

Before describing the invention in greater detail, the following definitions are set forth to illustrate and define the meaning and scope of the terms used to describe the invention herein.

As used herein, "subject" refers to any mammal, including humans, bovines, ovines, porcines, canines and felines. In some embodiments, the subject is a human.

As used herein, "visceral adipose tissue" or "visceral fat" is defined as the fat in the abdominal region which is inside the peritoneal cavity, and thus is distinct from "subcutaneous adipose tissue" or "subcutaneous fat". Visceral fat can be assessed, either qualitatively or quantitatively, by standard assays known to one of ordinary skill in the art, for example, by computer tomography (CT) scan.

Changes in visceral fat levels in a subject (i.e., a "decrease in visceral fat") can be approximated by a subject's waist to hip measurement ratio. The waist measurement (or "abdominal perimeter") takes into account both visceral and subcutaneous fat, while the hip measurement takes into account only subcutaneous fat. A reduction in visceral fat in a subject having visceral obesity can be approximated by, for example, reduction of a waist to hip measurement ratio from greater than about 1 (where the measurement of the waist circumference and the measurement of the hip circumference are about the same) to a ratio of less than about 1 (wherein the measurement of the waist circumference is less than the measurement of the hip circumference). A reduction in visceral fat in a viscerally obese subject can also be determined by, for example, a reduction in the waist to hip measurement ratio of greater than about 2%, including about 3% to about 100%, such as by about 4% to about 98%. In general, a decrease in the waist measurement greater than the decrease in hip measurement indicates that visceral fat is reduced in the subject. For example, a decrease in visceral fat is determined where the waist diameter measurement decreases by at least about 1 cm more than the hip measurement, at least about 2 cm or more than the hip measurement, e.g., about 3 cm to about 5 cm or more than the hip measurement.

As used herein, "subcutaneous fat" is defined as fat deposited just under the skin, e.g., under the skin of the thigh area.

As used herein, "redistributing body fat" means decreasing visceral fat in relation to subcutaneous fat, i.e., reducing the ratio of visceral fat to subcutaneous fat. Redistribution of body fat is, without being held to theory, one possible explanation for reduction of visceral fat in a subject without a proportional reduction in body weight or BMI, which may be due to, for example, a proportional or non-proportional increase in subcutaneous fat.

A reduction in the ratio of visceral fat to subcutaneous fat in a subject having visceral obesity can be approximated by, for example, reduction of a waist to hip measurement ratio from greater than about 1 (where the measurement of the waist circumference and the measurement of the hip circumference are about the same) to a ratio of less than about 1 (wherein the measurement of the waist circumference is less than the measurement of the hip circumference). A reduction in the ratio of visceral fat to subcutaneous fat in a subject can also be determined by, for example, a reduction in the waist to hip measurement ratio of greater than about 2%, including about 3% to about 100%, such as by about 4% to about 98%. In general, a decrease in the waist measurement greater than the decrease in hip measurement indicates that the ratio of visceral fat to subcutaneous fat is reduced in the subject. For example, a decrease in the ratio of visceral fat to subcutaneous fat is determined where the waist diameter measurement decreases by at least about 1 cm more than the hip measurement, at least about 2 cm or more than the hip measurement, e.g., about 3 cm to about 5 cm or more than the hip measurement.

As used herein, "IGF-I" refers to insulin-like growth factor-I from any species, including bovine, ovine, porcine, equine, avian, and preferably human, in native-sequence or in variant form, and from any source, whether natural, synthetic, or recombinant.

Suitable for use in the subject methods is human native-sequence, mature IGF-I, for example, without a N-terminal methionine, prepared, e.g., by the process described in EP 230,869 published Aug. 5, 1987; EP 128,733 published Dec. 19, 1984; or EP 288,451 published Oct. 26, 1988. In some embodiments, this native-sequence IGF-I is recombinantly produced, see for example, EP 123,228 and 128,733. rhIGF-I refers to recombinant, human IGF-I.

As used herein, reference to "variants" or "analogs, homologs and mimics" of IGF-I includes compounds which differ from the structure of native IGF-I by as little as the replacement and/or deletion of one or more residues thereof, to compounds which have no apparent structural similarity. Such compounds in all instances, however, have substantially the same activity as native IGF-I. Thus, "analogs" refers to compounds having the same basic structure as IGF-I, but differing in several residues; "homologs" refers to compounds which differ from native IGF-I by the deletion and/or replacement of a limited number of residues; and "mimics" refers to compounds which have no specific structural similarity with respect to IGF-I (for example, a mimetic of IGF-I need not even be a polypeptide), but such compound will display the biological activity characteristic of IGF-I and/or stimulate endogenous IGF-I production by the body.

Suitable for use in the present invention are IGF-I variants described in U.S. Pat. No. 5,077,276 issued Dec. 31, 1991; U.S. Pat. Nos. 5,164,370; 5,470,828; in PCT WO 87/01038 published Feb. 26, 1987 and in PCT WO 89/05822 published Jun. 29, 1989, i.e., those wherein at least the glutamic acid residue is absent at position 3 from the N-terminus of the mature molecule or those having a deletion of up to five amino acids at the N-terminus. In some embodiments, the IGF-I variant for use in the subject methods has the first three amino acids from the N-terminus deleted (variously designated as brain IGF, tIGF-I, des(1-3)-IGF-I, or des-IGF-I).

As used herein, an "IGF binding protein" or "IGFBP" refers to a protein or polypeptide normally associated with or bound or complexed to IGF-I or IGF-2, whether or not polypeptide is circulatory (i.e., present in serum or tissue). Such "IGF binding proteins" do not include receptors. The term "IGF binding protein" includes, for example, IGFBP-1, IGFBP-2, IGFBP-3, IGFBP-4, IGFBP-5, IGFBP-6, Mac 25 (IGFBP-7), and prostacyclin-stimulating factor (PSF) or endothelial cell-specific molecule (ESM-1), as well as other proteins with high homology to IGFBPs. Mac 25 is described, for example, in Swisshelm et al., 1995, Proc Natl Acad Sci USA, 92: 4472-4476 and Oh et al., J Biol Chem, 271: 30322-30325 (1996). PSF is described in Yamauchi et al., 1994, Biochem J, 303:591-598. ESM-1 is described in Lassalle et al., 1996, J Biol Chem, 271: 20458-20464. For other identified IGFBPs, see, e.g., EP 375,438 published Jun. 27, 1990; EP 369,943 published May 23, 1990; WO 89/09268 published Oct. 5, 1989; Wood et al., 1988, Mol Endocrinol, 2: 1176-1185; Brinkman et al., 1988, EMBO J, 7: 2417-2423; Lee et al., 1988, Mol Endocrinol, 2:404-411; Brewer et al., 1988, Biochem Biophys Res Comm, 152: 1289-1297; EP 294,021 published Dec. 7, 1988; Baxter et al., 1987, Biochem Biophys Res Comm, 147: 408-415; Leung et al., 1987, Nature, 330: 537-543; Martin et al., 1986, J Biol Chem, 261:8754-8760; Baxter et al., 1988, Comp Biochem Physiol, 91B: 229-235; WO 89/08667 published Sep. 21, 1989; WO 89/09792 published Oct. 19, 1989; and Binkert et al., 1989, EMBO J, 8: 2497-2502.

As used herein, "active", "bioactive", "biologically active" or "free" IGF-I in the context of changing serum and tissue levels of endogenous IGF-I refers to an unbound IGF-I that is capable of binding to an IGF or insulin receptor, or a hybrid IGF/insulin receptor, or to an IGF binding protein, or is otherwise capable of causing a biological activity of endogenous or exogenous IGF-I to occur.

A "compound that increases the bioactive serum levels of IGF-I" refers to any compound that results in increased serum levels of free or bioavailable IGF-I which is capable of activating an IGF receptor. Such compounds include, for example, compounds that inhibit or prevent the interaction of IGF-I with any one of its IGFBPs, compounds that increase expression fIGF-I, compound that inhibits or prevents clearance of bioavailable IGF-I, and the like.

A compound that "inhibits" or "prevents" the interaction of IGF-I with any one of its IGFBPs refers to a molecule that increases serum and/or tissue levels of biologically active IGF-I, no matter how this increase occurs. For instance, the compound may partially or completely displace active IGF from a complex in which the IGF is bound to one or more of its IGFBPs, i.e., is an IGF-I displacer. The compound under this definition may bind to an IGFBP, and possibly thereby act to displace an endogenous IGF formerly bound to the IGFBP, or it may bind to an IGF itself at a site remote from that involved in receptor interactions so as to inhibit or prevent the interaction of the IGF with one or more of its IGFBPs, but not inhibit or prevent the interaction of the IGF with any of its receptors. Further, while the compound will occupy the IGFBPs, the effect on the ternary complex will depend on whether the binary complexes can form ternary ones.

As used herein, "obesity" refers to a condition, as defined by the United States Centers for Disease Control, which is presently defined as an adult subject (a subject of about 20 years of age or older) presents with a body-mass index (BMI)

of about 30 or greater. It will be readily appreciated by the ordinarily skilled artisan in the field that the BMI-based definition of obesity may be modified to reflect changes in understanding of the condition or practices in the field, and such changes to the BMI-based definition of obesity are contemplated herein. For subjects of about 2 to 20 years in age, obesity is determined using a BMI-for-age calculation, which is plotted on gender specific growth charts (such as those available from the United States Centers for Disease Control (see, e.g., the World Wide Web site of cdc.gov/growthcharts/)). A change in BMI of about 0.5 or 1 is considered significant.

"Visceral obesity" refers to obesity that is associated with an excess of visceral fat, e.g., the ratio of visceral fat to subcutaneous fat is higher in the individual than that of a normal person or a person having obesity primarily attributed to subcutaneous fat. For example, a subject is viscerally obese where the subject has a waist to hip measurement ratio that is greater than about 1.

"Overweight" refers to a condition wherein an adult subject (a subject of about 20 years of age or older) presents with a body-mass index (BMI) of about 25 or greater. It will be readily appreciated by the ordinarily skilled artisan in the field that the BMI-based definition of overweight may be modified to reflect changes in understanding of the condition or practices in the field, and such changes to the BMI-based definition of overweight are contemplated herein. For subjects of about 2 to 20 years in age, obesity is determined using a BMI-for-age calculation, which is plotted on gender specific growth charts (such as those available from the United States Centers for Disease Control (see, e.g., the World Wide Web site of cdc.gov/growthcharts/)).

As used herein, "IGF-I deficient" means any condition wherein the subject has IGF-I levels below the normal range for their age and gender. An IGF-I deficiency can result from genetic abnormality or can result of a disease or disorder which causes a deficit or decrease in IGF-I production. Normal levels of IGF-I in children are provided in, for example, Juul A, 2001, Horm Res, 55 Suppl 2:94-9. Normal ranges for free IGF-I serum levels, categorized by age and gender, are provided in Juul A et al., 1997, J Clin Endocrinol Metab 82:2497-2502.

As used herein, "short stature" means a subject who has a height standard deviation score of about $\leq 2$ SD below normal for the same age and gender.

As used herein, "ameliorating a symptom" refers to an improvement of at least one discernible symptom or at least one measurable physical parameter of a disease or disorder, e.g., obesity or IGF-I deficiency-related condition, for example, at least one discernible symptom or at least one measurable physical parameter of cardiovascular disease.

As used herein, "ameliorating visceral fat deposition" refers to a decrease in visceral fat deposition or existing visceral fat as measured by standard techniques, such as waist to hip measurement ratio, waist measurement, or CT abdominal scans, as compared to an absence of treatment. Ameliorating visceral fat deposition can be determined by, for example, a reduction in the waist to hip measurement ratio by about from 1 to less than 1, such as from about 1.0 to about 0.98 or less, including from about from 1.0 to about 0.95 or less, 0.90 or less, and 0.80 or less.

As used herein, "treatment" or "treating" refers to inhibiting the progression of a disease or disorder, e.g., visceral obesity, or delaying the onset of a disease or disorder, e.g., visceral obesity, whether physically, e.g., stabilization of a discernible symptom, physiologically, e.g., stabilization of a physical parameter, or both. As used herein, the terms "treatment," "treating," and the like, refer to obtaining a desired pharmacologic and/or physiologic effect. The effect may be prophylactic in terms of completely or partially preventing a disease or condition, or a symptom thereof and/or may be therapeutic in terms of a partial or complete cure for a disease or disorder and/or adverse affect attributable to the disease or disorder. "Treatment," as used herein, covers any treatment of a disease or disorder in a mammal, such as a human, and includes: decreasing the risk of death due to the disease; preventing the disease of disorder from occurring in a subject which may be predisposed to the disease but has not yet been diagnosed as having it; inhibiting the disease or disorder, i.e., arresting its development (e.g., reducing the rate of disease progression); and relieving the disease, i.e., causing regression of the disease. Therapeutic benefits of the present invention include, but are not necessarily limited to, reduction of risk of onset or severity of disease or conditions associated visceral obesity, improvements in appearance (e.g., the therapy is a "cosmetically effective" therapy, which may be further associated with improved physical appearance, psychological benefits, emotional benefits, and the like).

As used herein, "prevention", "preventing" or "prophylactic" refers to a reduction in a subject's risk of acquiring a disease or disorder, e.g., visceral obesity, wherein the subject has either a genetic predisposition to visceral obesity (e.g., which may or may not be associated with an IGF-I deficiency-related condition), such as a family history of the disease, or a non-genetic predisposition to visceral obesity.

As used herein, a "therapeutically effective amount" refers to that amount of the compound sufficient to treat or manage a disease or disorder, e.g., visceral obesity, as determined by a clinician or a physician. A therapeutically effective amount may refer to the amount of a compound sufficient to delay or minimize the onset of disease, e.g., delay or minimize the onset of visceral obesity and/or a condition associated with visceral obesity. A therapeutically effective amount may also refer to the amount of a compound that provides a therapeutic benefit in the treatment or management of a disease. Further, a therapeutically effective amount with respect to a compound of the invention means that amount of compound alone, or in combination with other therapies, that provides a therapeutic benefit in the treatment or management of a disease. The term can encompass, for example, an amount that improves overall therapy, reduces or avoids unwanted effects, enhances the therapeutic efficacy of or synergies with another therapeutic agent, and the like.

In some embodiments, "therapeutically effective amount" may also encompass a "cosmetically effective amount" as determined by a clinician or a physician, and refers to the amount of a compound sufficient to improve the outward physical appearance of a subject. The outward physical appearance of a subject may include, for example, the reduction of fat deposition in certain regions of the body including, for example, the midsection of the body.

As used herein, the term "hyperglycemic disorders" refers to any disorder known in the art in which insulin production, secretion or function (i.e., insulin resistance) is altered in an individual, such as, for example, diabetes and disorders resulting from insulin resistance, such as Type I and Type II diabetes, as well as severe insulin resistance, hyperinsulinemia, gestational diabetes, autoimmune diabetes, hyperglycemia, β-cell failure, insulin resistance, dyslipemias, atheroma and insulinoma, and hyperlipidemia, e.g., obese subjects, and insulin-resistant diabetes, such as Mendenhall's Syndrome, Werner Syndrome, leprechaunism, lipoatrophic diabetes, and other lipoatrophies. "Diabetes" itself refers to a progressive disease of carbohydrate metabolism involving inadequate production or utilization of insulin and is characterized by hyperglycemia and glycosuria.

As used herein, "growth-promoting agents" are reagents that promote growth in a mammal. Such reagents include, but are not limited to, growth hormone (GH) secretagogues that promote the release of endogenous GH in mammals that result in increased concentrations of IGF in the serum. Examples include TRH, diethylstilbestrol, theophylline, enkephalins, E series prostaglandins, peptides of the VIP-secretin-glucagon-GRF family, and other GH secretagogues such as GHRP-6, GHRP-1 as described in U.S. Pat. No. 4,411,890, and benzo-fused lactams such as those disclosed in U.S. Pat. No. 5,206,235. See also, e.g., WO 96/15148 published May 23, 1996. Other growth-promoting agents include growth hormone releasing peptides (GHRPs), growth hormone releasing hormones (GHRHs), GH, long-acting GH, GH plus GHBP, and their analogs. For example, GHRPs are described in WO 95/17422 and WO 95/17423 both published Jun. 29, 1995; Bowers, J, 1993, Pediatr Endocrinol, 6:21-31; and Schoen et al., 1993, Annual Reports in Medicinal Chemistry, 28: 177-186. GHRHs and their analogs are described, for example, in WO 96/37514 published Nov. 28, 1996. Additional growth-promoting agents include IGF-2, or if a compound other than IGF-I is employed, IGF-I or IGF-I with an IGFBP such as IGF-I complexed to IGFBP-3. For example, pharmaceutical compositions containing IGF-I and IGFBP in a carrier as described in WO 94/16723 published Aug. 4, 1994 can be used in conjunction with the compound that is not IGF-I itself.

As used herein, the term "hypoglycemic agent" refers to compounds that are useful for regulating glucose metabolism, such as oral agents. In some embodiments, such agents for human use include insulin and the sulfonylurea class of oral hypoglycemic agents, which cause the secretion of insulin by the pancreas. Examples include glyburide, glipizide, and gliclazide. In addition, agents that enhance insulin sensitivity or are insulin sensitizing, such as biguanides (including metformin and phenformin) and thiazolidenediones such as REZULIN™ (troglitazone) brand insulin-sensitizing agent, and other compounds that bind to the PPARgamma nuclear receptor, are within this definition.

As used herein, "insulin" refers to any type of insulin from any species, including bovine, ovine, porcine, equine, and preferably human, and from any source, whether natural, synthetic, or recombinant. All insulin drugs reported, for example, in Diabetes Mellitus—Theory and Practice, fourth edition, Harold Rifkin, MD, Ed. (Elsevier, N.Y., 1990), Chapter 29, and U.S. Pharmacist, 18 (November Suppl.) p. 3840 (1993) are suitable herein. All the various forms of human insulin on the market are included, such as those mentioned in Jens Brange, Galenics of Insulin. The Physico-chemical and Pharmaceutical Aspects of Insulin and Insulin Preparations (Springer-Verlag, N.Y., 1987), page 17-40. These include Regular insulin, NPH (Neutral Protamine Hagedom) insulin, also called Isophane Insulin, 70/30 insulin, composed of 70% NPH-insulin and 30% Regular insulin, Semilente insulin, UltraLente insulin, Lente insulin, and Humalog insulin.

As used herein, a "pharmaceutical composition" is meant to encompass a composition suitable for administration to a subject, such as a mammal, especially a human. In general a "pharmaceutical composition" is sterile, and preferably free of contaminants that are capable of eliciting an undesirable response within the subject (e.g., the compound(s) in the pharmaceutical composition is pharmaceutical grade). Pharmaceutical compositions can be designed for administration to subjects or patients in need thereof via a number of different routes of administration including oral, buccal, rectal, parenteral, intraperitoneal, intradermal, intracheal and the like. In some embodiments the composition is suitable for administration by a transdermal route, using a penetration enhancer other than DMSO. In other embodiments, the pharmaceutical compositions are suitable for administration by a route other than transdermal administration.

As used herein, the phrase "pharmaceutically acceptable carrier" refers to a carrier medium that does not interfere with the effectiveness of the biological activity of the active ingredient. Said carrier medium is essentially chemically inert and nontoxic.

As used herein, the phrase "pharmaceutically acceptable" means approved by a regulatory agency of the Federal government or a state government, or listed in the U.S. Pharmacopeia or other generally recognized pharmacopeia for use in animals, and more particularly for use in humans.

As used herein, the term "carrier" refers to a diluent, adjuvant, excipient, or vehicle with which the therapeutic is administered. Such carriers can be sterile liquids, such as saline solutions in water, or oils, including those of petroleum, animal, vegetable or synthetic origin, such as peanut oil, soybean oil, mineral oil, sesame oil and the like. A saline solution is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The carrier, if desired, can also contain minor amounts of wetting or emulsifying agents, or pH buffering agents. These pharmaceutical compositions can take the form of solutions, suspensions, emulsion, tablets, pills, capsules, powders, sustained-release formulations and the like. The composition can be formulated as a suppository, with traditional binders and carriers such as triglycerides. Examples of suitable pharmaceutical carriers are described in *Remington's Pharrmaceutical Sciences* by E. W. Martin. Examples of suitable pharmaceutical carriers are a variety of cationic polyamines and lipids, including, but not limited to N-(1(2,3-dioleyloxy)propyl)-N,N,N-trimethylammonium chloride (DOTMA) and diolesylphosphotidylethanolamine (DOPE). Liposomes are suitable carriers for gene therapy uses of the invention. Such pharmaceutical compositions should contain a therapeutically effective amount of the compound, together with a suitable amount of carrier so as to provide the form for proper administration to the subject. The formulation should suit the mode of administration.

As used herein, "pharmaceutically acceptable derivatives" of a compound of the invention include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs.

As used herein, the phrase "pharmaceutically acceptable salts" refers to salts prepared from pharmaceutically acceptable, essentially nontoxic, acids and bases, including inorganic and organic acids and bases. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

"In combination with" as used herein refers to uses where, for example, the first compound is administered during the entire course of administration of the second compound; where the first compound is administered for a period of time that is overlapping with the administration of the second compound, e.g. where administration of the first compound begins before the administration of the second compound and the administration of the first compound ends before the administration of the second compound ends; where the administration of the second compound begins before the administration of the first compound and the administration of the second compound ends before the administration of the first compound ends; where the administration of the first compound begins before administration of the second compound begins and the administration of the second compound ends before the administration of the first compound ends; where the administration of the second compound begins before administration of the first compound begins and the administration of the first compound ends before the administration of the second compound ends. As such, "in combination" can also refer to regimen involving administration of two or more compounds. "In combination with" as used herein also refers to administration of two or more compounds which may be administered in the same or different formulations, by the same of different routes, and in the same or different dosage form type.

It is further noted that the claims may be drafted to exclude any optional element. As such, this statement is intended to serve as antecedent basis for use of such exclusive terminology as "solely", "only" and the like in connection with the recitation of claim elements, or the use of a "negative" limitation.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an," and "the" include plural referents unless the context clearly dictates otherwise. Thus, for example, reference to "an individual" includes one or more individuals, and reference to "the method" includes reference to equivalent steps and methods known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed. Citation or discussion of a reference herein shall not be construed as an admission that such is prior art to the present invention.

The practice of the present invention will employ, unless otherwise indicated, conventional methods of chemistry, biochemistry, recombinant DNA techniques and virology, within the skill of the art. Such techniques are explained fully in the literature. See, e.g., Fundamental Virology, 2nd Edition, vol. I & II (B. N. Fields and D. M. Knipe, eds.); A. L. Lehninger, Biochemistry (Worth Publishers, Inc., current addition); Sambrook, et al., Molecular Cloning: A Laboratory Manual (2nd Edition, 1989); Methods In Enzymology (S. Colowick and N. Kaplan eds., Academic Press, Inc.); Oligonucleotide Synthesis (N. Gait, ed., 1984); A Practical Guide to Molecular Cloning (1984).

The invention will now be described in more detail.

DETAILED DESCRIPTION OF THE INVENTION

The present invention is based on the surprising finding that IGF-I administration in humans decreased visceral fat, so as to provide the subject with an improved body fat distribution (e.g., the subject after treatment had a decreased ratio of visceral to subcutaneous body fat). It is an object of the present invention to provide methods and compositions for decreasing visceral fat. In one embodiment, a compound suitable for use in the subject methods comprises a visceral fat decreasing agent, a visceral fat accumulation inhibitor, or a body fat distribution improver each of which comprises a compound which increases bioactive IGF-I levels. In a further embodiment, the compound comprises IGF-I. In certain embodiments, IGF-I is administered in combination with other hypoglycemic agents as an active ingredient. In certain embodiments, as in the case of IGF-I deficient subjects, the goal of treatment is to restore IGF-I levels to those found within normal subjects of the same age and gender.

Without being bound by any theory, in IGF-I deficient subjects, increasing the levels of blood or tissue IGF-I would be expected to act to reduce the amount of visceral fat or the accumulation of visceral fat preventing the side effects of excess visceral fat including the metabolic, cardiovascular, and lipid abnormalities of obesity. This increase in visceral fat could be due to accumulation due to the progression of a disease, such as in subjects with diabetes. An example of a prophylactic use of IGF-I is in young obese children (those who develop Type II diabetes at a young age). In such subjects, IGF-I will prevent the accumulation of visceral body fat. Thus, in certain aspects, the present invention relates to methods for the treatment, diagnosis, prevention, or amelioration of one or more symptoms or conditions affected by excessive visceral fat.

Increasing IGF-I Levels

The present invention provides methods and compositions for reducing visceral fat in a subject, comprising administering to the subject a compound which increases bioactive IGF-I serum levels. The methods of the present invention can be achieved by the administration of any compound that increases bioactive IGF-I serum levels, with the proviso that growth hormone is not used.

IGF-I naturally occurs in human body fluids, for example, blood and human cerebral spinal fluid and in human tissues. Although IGF-I is produced in many tissues, most circulating IGF-I is believed to be synthesized in the liver. The IGFBPs are believed to modulate the biological activity of IGF-I (See Jones and Clemmons, 1995, Endocr Rev, 16:3-34), with IGFBP-1 (See Lee et al., 1993, Proc Soc Exp Biol & Med, 204:4-29) being implicated as the primary binding protein involved in regulating glucose metabolism. See Baxter, "Physiological roles of IGF binding proteins", in: Spencer (Ed.), Modern Concepts of Insulin-like Growth Factors (Elsevier, New York, 1991), pp. 371-380. IGFBP-1 production by the liver is regulated by nutritional status, with insulin directly suppressing its production. See Suikkari et al., 1988, J Clin Endocrinol Metab, 66: 266-272.

Unlike most other growth factors, the IGFs are present in high concentrations in the circulation, but only a small fraction of the IGFs is not protein bound. For example, it is generally known that in humans or rodents, less than 5% of the IGFs in blood is normally in a "free" or unbound form. See Juul et al., 1996, Clin Endocrinol, 44: 515-523; Hizuka et al., 1991, Growth Regulation, 1: 51-55; Hasegawa et al., 1995, J Clin Endocrinol Metab, 80: 3284-3286. The overwhelming majority of the IGFs in blood circulate as part of a non-covalently associated ternary complex composed of IGF-I or IGF-2, IGFBP-3, and a large protein termed the acid-labile subunit (ALS). This complex is composed of equimolar amounts of each of the three components. The ternary complex of an IGF, IGFBP-3, and ALS has a molecular weight of approximately 150,000 daltons, and it has been suggested that the function of this complex in the circulation may be to serve as a reservoir and buffer for IGF-I and IGF-2, preventing rapid changes in free IGF-I or IGF-2.

Thus, in some embodiments, increasing the levels of bioactive IGF-I can be achieved by using a molecule that displaces IGF-I that is bound to IGFBPs. In other embodiments, increasing the levels of IGF-I can be achieved by direct administration of IGF-I, such as native human IGF-1 or recombinant human IGF-I (rhIGF-I) or a variant or analog thereof. In another embodiment, increasing the levels of IGF-I can be achieved by direct administration of a complex of IGF-I bound to an IGFBP, such as IGFBP-3, is used.

Suitable for use in the subject methods are IGF-I variants. IGF-I variants can be designed that retain efficient binding to the type I receptor, yet would have reduced binding to serum carrier proteins, e.g. IGFBPs. In one aspect, the design of these variants is based on the observation that insulin does not bind to serum carrier proteins. See U.S. Pat. No. 4,876,242, issued Oct. 24, 1989, herein expressly incorporated by reference in its entirety. Evidence from synthetic, insulin-like two chain analogs suggests that amino acids of IGF-I responsible for carrier protein binding are in the B region of IGF-I. Therefore a synthetic gene for human IGF-I can be modified to encode an IGF-I variant in which the first 16 amino acids of hIGF-I are replaced by the first 17 amino acids of the B chain of human-insulin. The synthetic gene is then placed in a yeast recombinant DNA expression system and the peptide analog which is produced by the modified yeast cells is extracted therefrom and purified. Additional modifications of the IGF-I molecule have been carried out leading to additional analogs, all of which have substantial IGF-I type I receptor binding and reduced binding to serum carrier proteins.

Other IGF-I variants and analogs well known in the art are also suitable for use in the subject methods. Such variants include, for example, the variant having residues 1-69 of authentic IGF-I, further described in WO 96/33216, the two-chain IGF-I superagonists which are derivatives of the naturally occurring single-chain IGF-I having an abbreviated C domain, further described in EP 742,228, Such IGF-I variants and analogs are of the formula: $BC^nA$ wherein B is the B domain of IGF-I or a functional analog thereof, C is the C domain of IGF-I or a functional analog thereof, n is the number of amino acids in the C domain and is from about 6 to about 12 amino acids, including about 8 to about 10, and A is the A domain of IGF-I or a functional analog thereof.

Also suitable for use in the subject methods are functional mutants of IGF-I that are well known in the art. Such functional mutants include those described in Cascieri et al. (1988, Biochemistry 27:3229-3233), which discloses four mutants of IGF-I, three of which have reduced affinity to the Type I IGF receptor. These mutants are: $(Phe^{23}, Phe^{24}, Tyr^{25})$ IGF-I (which is equipotent to human IGF-I in its affinity to the Types 1 and 2 IGF and insulin receptors), $(Leu^{24})$IGF-I and $(Ser^{24})$IGF-I (which have a lower affinity than IGF-I to the human placental Type I IGF receptor, the placental insulin receptor, and the Type I IGF receptor of rat and mouse cells), and desoctapeptide $(Leu^{24})$IGF-I (in which the loss of aromaticity at position 24 is combined with the deletion of the carboxyl-terminal D) region of hIGF-I, which has lower affinity than $(Leu^{24})$IGF-I for the Type I receptor and higher affinity for the insulin receptor). These four mutants have normal affinities for human serum binding proteins.

Also suitable for use with the subject methods include structural analogs of IGF-I well known in the art. Such structural analogs include those described in Bayne et al. (1988, J Biol Chem 264:11004-11008), which discloses three structural analogs of IGF-I: (1-62)IGF-I, which lacks the carboxyl-terminal 8-amino-acid D region of IGF-I; $(1-27,Gly^4, 38-70)$IGF-I, in which residues 28-37 of the C region of IGF-I are replaced by a four-residue glycine bridge; and $(1-27,Gly^4, 38-62)$ IGF-I, with a C region glycine replacement and a D region deletion. Peterkofsky et al. (1991, Endocrinology, 128: 1769-1779) discloses data using the $Gly^4$ mutant of Bayne et al., supra. U.S. Pat. No. 5,714,460 refers to using IGF-I or a compound that increases the active concentration of IGF-I to treat neural damage.

Other structural analogs include those described in Cascieri et al. (1989, J Biol Chem, 264: 2199-2202), which discloses three IGF-I analogs in which specific residues in the A region of IGF-I are replaced with the corresponding residues in the A chain of insulin. The analogs are: $(Ile^{41}, Glu^{45}, Gln^{46}, Thr^{49}, Ser^{53}, Ile^{51}, Ser^{53}, Tyr^{55}, Gln^{56})$IGF-I, an A chain mutant in which residue 41 is changed from threonine to isoleucine and residues 42-56 of the A region are replaced; $(Thr^{49},Ser^{50},Ile^{51})$IGF-I; and $(Tyr^{55}, Gln^{56})$IGF-I.

IGF-I point variants which bind to IGFBP-1 or IGFBP-3, thus inhibiting the interaction of endogenous IGF-I with IGFBPs are also suitable for use with the subject methods and are described in U.S. Pat. No. 6,509,443.

In another embodiment, the level of IGF-I is increased by administering a compound that prevents or inhibits the interaction of IGF-I with its binding proteins, such as a IGF-I agonist molecules that are capable of effectively inhibiting the interaction of IGF-I with its binding proteins, thereby allowing IGF-I to bind to the IGF receptor for activity. Such IGF-I agonists suitable for use in the subject methods include those described in, for example, U.S. Pat. Nos. 6,251,865; 6,420,518; and 6,121,416, all of which are hereby expressly incorporated by reference in their entireties, along with WO 98/45427 published Oct. 15, 1998 and Lowman et al., 1998, Biochemistry, 37:8870-8, which disclose IGF-I agonists identified by phage display. These IGF-I agonist molecules can effectively displace IGF-I bound to IGFBP. The IGF binding proteins (IGFBPs) are a family of at least six proteins (See Jones and Clemmons, 1995, Endocr Rev, 16: 3-34; Bach and Rechler, 1995, Diabetes Reviews, 3: 38-61), with other related proteins also possibly binding the IGFs. The IGFBPs bind IGF-I and IGF-2 with varying affinities and specificities. See Jones and Clemmons, supra; Bach and Rechler, supra. For example, IGFBP-3 binds IGF-I and IGF-2 with a similar affinity, whereas IGFBP-2 and IGFBP-6 bind IGF-2 with a much higher affinity than they bind IGF-I. See Bach and Rechler, supra; Oh et al., 1993, Endocrinology, 132, 1337-1344.

Also suitable for use with the subject methods include binding molecules, other than a natural IGFBP, as described in WO 94/04569, that can prevent the binding of IGF-I to a IGFBP by binding to IGF-I and thereby enhancing the biological activity of IGF-I. In addition, other molecules that are capable of preventing or inhibiting the interaction of IGF-I with its binding proteins includes ligand inhibitors of IGF-I, as disclosed in WO 97/39032.

Small molecule nonpeptide inhibitors can also release biologically active IGF-I from the IGF-I/IGFBP-3 complex. For example, isoquinoline analogues have been found to be effective (See Chen et al., 2001, J Med Chem 44:4001-10). Additional compounds can be found using high throughput screening and the IGFBP Radioligand binding assay as described Chen et al., 2001.

Other IGF-I agonists include, but are not limited to; small molecules; synthetic drugs; peptides; polypeptides; proteins; nucleic acids (e.g., DNA and RNA nucleotides including, but not limited to, antisense nucleotide sequences, triple helices and nucleotide sequences encoding biologically active proteins, polypeptides or peptides); antibodies; synthetic or natural inorganic molecules; mimetic agents; and synthetic or natural organic molecules.

In another embodiment of the invention, IGF-I levels are increased by nutritional supplements. For example, the administration of L-acetylcamitine, L-isovalerylcarnitine, L-propionylcamitine or pharmacologically acceptable salts thereof is capable of inducing the production of IGF-I without the undesirable effects produced by the administration of exogenous IGF-I. See U.S. Pat. No. 6,380,252, issued Apr. 30, 2002, herein expressly incorporated by reference in its entirety.

According to another embodiment of the present invention, the administration of any of L-acetylcarnitine, L-isovaleryl-camitine, L-propionylcarnitine or pharmacologically acceptable salts thereof in combination with any of L-carnitine, coenzyme Q10, vitamin E and/or Se-L-methionine and pharmaceutically acceptable salts and derivatives thereof can lead to increased IGF-I levels.

In addition, the present invention contemplates using gene therapy for treating a mammal to increase IGF-I levels. Generally, gene therapy can be used to increase (or overexpress) IGF-I levels in the mammal using a recombinant vector to express an IGF-I gene. Also, gene therapy can be used to express a nucleic acid encoding an IGF agonist compound, if it is a peptide. As another example, antisense oligonucleotides can be used to reduce the expression of an IGFBP. Other examples of gene therapy can be contemplated by one of routine skill in the art.

There are two major approaches to introducing the nucleic acid (optionally contained in a vector) into the subject's cells for purposes of gene therapy: in vivo and ex vivo. For in vivo delivery, the nucleic acid is injected directly into the subject, usually at the site where increased levels of IGF-I is required. For ex vivo treatment, the subject's cells are removed, the nucleic acid is introduced into these isolated cells and the modified cells are administered to the subject either directly or, for example, encapsulated within porous membranes which are implanted into the subject. See, e.g. U.S. Pat. Nos. 4,892,538 and 5,283,187, both of which are herein expressly incorporated by reference in their entireties.

There are a variety of techniques available for introducing nucleic acids into viable cells. The techniques vary depending upon whether the nucleic acid is transferred into cultured cells in vitro, or in vivo in the cells of the intended host. Techniques suitable for the transfer of nucleic acid into mammalian cells in vitro include the use of liposomes, electroporation, microinjection, cell fusion, DEAE-dextran, the calcium phosphate precipitation method, etc. A commonly used vector for ex vivo delivery of the gene is a retrovirus.

An example of a in vivo nucleic acid transfer technique includes transfection with viral vectors (such as adenovirus, Herpes simplex I virus, or adeno-associated virus) and lipid-based systems (useful lipids for lipid-mediated transfer of the gene are DOTMA, DOPE and DC-Chol, for example). In some situations it is desirable to provide the nucleic acid source with an agent that targets the target cells, such as an antibody specific for a cell surface membrane protein or the target cell, a ligand for a receptor on the target cell, etc. Where liposomes are employed, proteins which bind to a cell surface membrane protein associated with endocytosis may be used for targeting and/or to facilitate uptake, e.g., capsid proteins or fragments thereof tropic for a particular cell type, antibodies for proteins which undergo internalization in cycling, and proteins that target intracellular localization and enhance intracellular half-life. The technique of receptor-mediated endocytosis is described, for example, by Wu et al., 1987, J Biol Chem, 262:4429-4432; and Wagner et al., 1990, Proc Natl Acad Sci USA, 87: 3410-3414. For a review of the currently known gene marking and gene therapy protocols, see Anderson et al., 1992, Science, 256: 808-813 and WO 93/25673 and the references cited therein.

Combination Therapy

Combination therapy with a compound that increases IGF-I levels and one or more other appropriate reagents, such as those that increase total IGF-I in the blood or enhance the effect of the IGF-I, is also contemplated by this invention. In one embodiment, these additional reagents generally allow an excess of serum IGF-I over the amount of IGFBPs in serum or the IGF-I to be released from IGFBPs, and include growth-promoting agents.

The reagent can be co-administered sequentially or simultaneously with the compound which increases IGF-I serum levels, and may be administered in the same, higher, or a lower dose than if used alone depending on such factors as, for example, the type of reagent used, the purpose for which the reagent and compound are being used, and clinical considerations. In addition, other means of manipulating IGF status, such as regimens of diet or exercise, are also considered to be combination treatments as part of this invention.

In some embodiments, the formulation is suitably administered along with an effective amount of a hypoglycemic agent, as defined herein, such as insulin or a sulfonylurea. The hypoglycemic agent is administered to the mammal by any suitable technique including parenterally, intranasally, orally, or by any other effective route. Most preferably, the administration is by the oral route. For example, MICRONASE™ tablets (glyburide) marketed by Upjohn in 1.25, 2.5, and 5 mg tablet concentrations are suitable for oral administration. The usual maintenance dose for Type II diabetics, placed on this therapy, is generally in the range of from or about 1.25 to 20 mg per day, which may be given as a single dose or divided throughout the day as deemed appropriate. See Physician's Desk Reference, 2563-2565 (1995): Other examples of glyburide-based tablets available for prescription include GLYNASE™ brand drug (Upjohn) and DIABETA™ brand drug (Hoechst-Roussel). GLUCOTROL™ (Pratt) is the trademark for a glipizide (1-cyclohexyl-3-(p-(2-(5-methylpyrazine carboxamide)ethyl)phenyl)sulfonyl)urea) tablet available in both 5- and 10-mg strengths and is also prescribed to Type II diabetics who require hypoglycemic therapy following dietary control or in subjects who have ceased to respond to other sulfonylureas. See Physician's Desk Reference, 1902-1903 (1995). Other hypoglycemic agents other than sulfonylureas, such as the biguanides (e.g., metformin and phenformin) or thiazolidinediones (e.g., troglitazone), or other drugs affecting insulin action may also be employed. If a thiazolidinedione is employed with the compound, it is used at the same level as currently used or at somewhat lower levels, which can be adjusted for effects seen with the compound alone or together with the dione. The typical dose of troglitazone (REZULIN™) employed by itself is about 100 to about 1000 mg per day, including about 200 to about 800 mg/day, such as about 300 to about 600 mg/day, and such ranges are applicable herein. See, for example, Ghazzi et al., 1997, Diabetes, 46: 433-439. In other embodiments, other thiazolidinediones that are stronger insulin-sensitizing agents than troglitazone may be employed in lower doses.

In some embodiments, where insulin is also administered, the insulin can be any formulation of insulin, such as, for example, NPH insulin, where the dose of NPH insulin is from about 5 to about 50 units/injection (i.e., from about 0.2 to about 2 mg) twice a day subcutaneously. For a combination of insulin and the compound, the ratio of NPH insulin to compound in this formulation by weight is generally from about 10:1 to about 1:50, including from about 1:1 to about 1:20, such as from about 1:1 to about 1:10, from about 1:1 to about 1:5, and from about 1:1 to about 1:3. The IGF-I can be formulated with insulin (see, e.g., U.S. Pat. Nos. 5,783,556 or 6,559,122).

In another embodiment, IGF-I is appropriately administered together with any one or more of its binding proteins, for example, IGFBP-1, IGFBP-2, IGFBP-3, IGFBP-4, IGFBP-5, or IGFBP-6. Without being bound by a mechanism, co-administration of IGF-I and an IGFBP may provide a greater response than IGF-I alone by increasing the half-life of IGF-I.

A binding protein suitable for use is IGFBP-3, which is described in U.S. Pat. No. 5,258,287 and by Martin and Baxter, 1986, J Biol Chem, 261: 8754-8760. This glycosylated IGFBP-3 protein is an acid-stable component of about 53 Kd on a non-reducing SDS-PAGE gel of a 125-150 Kd glycoprotein complex found in human plasma that carries most of the endogenous IGFs and is also regulated by GH.

The administration of the IGF binding protein with IGF-I may be accomplished by the method described in U.S. Pat. No. 5,187,151. Briefly, the IGF-I and IGFBP are administered in effective amounts by subcutaneous bolus injection in a molar ratio of from about 0.5:1 to about 3:1, including about 0.75:1 to about 2:1, such as about 1:1.

Certain medicaments induce fat deposition as a side effect of their activity. For example, protease inhibitors used in treating HIV can result in central fat distribution. See Hui, D Y, 2003, Prog Lipid Res 42:81-92. The administration of insulin, or a stimulation of insulin secretion or the administration of a compound that increases the sensitivity of insulin receptors in visceral adipose depots, also increases the deposition of fat in visceral fat depots (see Example 1). The co-administration of a compound that increases bioactive serum levels of IGF-I can ameliorate these side effects to reduce overall deposition or reduce the amount of visceral fat deposited.

Diseases or Conditions Associated with Visceral Obesity

Methods which reduce the ratio of visceral fat to subcutaneous fat in a subject with visceral obesity can be used to reduce the risk of diseases and conditions associated with visceral fat. Visceral fat is an important predictor of diseases and conditions such as coronary heart disease, certain cancers, diabetes, glucose intolerance and hyperinsulinemia. See Montague, C T et al., 2000, Diabetes 49:883-888. Without being bound by any particular theory, visceral fat is thought to put a greater fatty acid burden on the liver, resulting in many of the above conditions. In addition, body fat distribution has been shown to have a very important impact on longevity, especially on the gender difference in longevity, due to the greater degree of visceral adiposity in men. See Kissebah A H et al., 1994, Physiol Rev 74:761-811. Visceral fat accumulation has also been found to be a predictor of hypertension in obese men. See Watanabe et al., 2003, Clin Exp Hypertens 25:199-208. Visceral fat has also been associated with periodontal disease. See Wood N et al., 2003, J Clin Periodontol 30:321-327.

The importance of visceral fat extends to the effect of dieting or weight loss. In a weight-loss intervention trial in nondiabetic obese subjects, the decrease in visceral adipose tissue was the body composition change after weight loss that best predicted the improvement in insulin sensitivity. See Goodpaster, B H et al., 1999, Diabetes 48:839-847.

Moreover, IGF-I deficient individuals who are not yet centrally obese can be treated prophylactically to reduce propensity to deposition of visceral fat. Such treatment would be expected to reduce the risk of diseases and conditions associated with visceral fat. The importance of body fat distribution was highlighted by very recent evidence showing that it is not necessary to be obese to be at risk of developing Type II diabetes; an excess of visceral fat by itself predisposes to diabetes. Goodpaster et al. showed that elderly men and women with normal body weight are at risk for metabolic abnormalities, including type II diabetes, if they possess a disproportionate amount of visceral abdominal fat. See Goodpaster, B H et al., 2003 Diabetes Care 26:372-379.

Obesity is one of the most powerful risk factor for type II diabetes. This is likely due to the associated insulin-resistant glucose metabolism in liver and skeletal muscle. For example, recent reports report an alarming increase in Type II diabetes in children, among Japanese schoolchildren type II diabetes was once rare, but is now seven times more common than type I diabetes, with its incidence increasing more than 30-fold over the past 20 years, which can be traced to changing diets and increased rates of obesity. See, e.g., Rosenbloom, A L, 1999, Diabetes Care 22:345-354. The relationship between obesity and insulin resistance has been has further dissected by studying the distribution of adipose tissue.

In one embodiment, the methods of the invention can reduce the ratio of visceral fat to subcutaneous fat, which may optionally be associated with induction of weight loss. In one embodiment, the methods of the invention also improve glucose control in diabetic subjects. U.S. Pat. No. 5,466,670, herein expressly incorporated by reference in its entirety, discusses that the normalization of IGF-I levels leads to better long term control of glucose levels. Proper glucose control can be measured by HbA1c levels. The U.S. Food and Drug Administration recognizes an endpoint of >5% for normal healthy individuals. In an alternative embodiment, the methods of the invention reduce the ratio of visceral fat to subcutaneous fat without necessarily inducing weight loss.

In yet another embodiment, the methods of the invention can reduce visceral fat (e.g., as assessed by the ratio of visceral fat to subcutaneous fat) and reduce the risk of heart disease in subjects with metabolic syndrome, a subset of diabetes. Metabolic syndrome is a condition associated with a subject having three or more of the following symptoms: excessive abdominal fat (in men, greater than 40-inch waist; in women, greater than 35-waist); high fasting blood glucose (110 mg/dL or higher); high fasting triglyceride levels (150 mg/dL or higher); low HDL (in men, less than 40 mg/dL; in women, less than 50 mg/dL); and high blood pressure (130/85 or higher).

In yet another embodiment, methods are provided for treatment, including prophylactic (prior to onset) and/or cosmetic treatment, of a subject, comprising administering a compound in an effective amount to reduce the amount of visceral fat and, in some instances, induce weight loss in the subject. In some instances weight loss is not reduced proportionately to the reduction in visceral fat (e.g., as assessed by the ratio of visceral fat to subcutaneous fat).

Subjects Suitable for Treatment

The methods of the present invention will aid those that have an excess of visceral fat, which may be reflected as a ratio of visceral fat to subcutaneous fat, or a percentage of total body fat that is attributed to visceral fat. In certain embodiments, the subjects are obese, diabetic or have an IGF-I deficiency.

Subjects who will benefit from increased IGF-I levels can be identified using routine methods known in the art. Visceral fat of subjects can be directly measured. Visceral obesity can be diagnosed by determining a subject's waist to hip measurement ratio. Generally, measurements are taken of the waist and hip and a ratio is compared to published tables which reflect the amount of risk for certain diseases or conditions associated with visceral obesity. The waist measurement, i.e., belt size, can also be used by itself. Changes in visceral fat levels in a subject (e.g., a "decrease in visceral fat") in response to treatment can be approximated by a subject's waist to hip measurement ratio. The waist measurement (or "abdominal perimeter") takes into account both visceral and subcutaneous fat, while the hip measurement takes into account only subcutaneous fat.

Visceral fat can be also assessed both qualitatively and quantitatively, by standard assays known to one of ordinary skill in the art, for example, by computer tomography (CT) scans of, for example, the abdomen. Where desired, CT scans can be used to assess both visceral and subcutaneous fat, as described in the Examples below. In such instances, it may be useful to determine the ratio of visceral fat to subcutaneous fat as part of determination of whether a subject is amenable to therapy, and/or to monitor therapy according to the invention.

In other embodiments, the subjects are IGF-I deficient, although an IGF-I deficiency need not be present for the subject to amenable to the therapy of the invention. In certain embodiments, the IGF-I deficient subjects are affected by visceral obesity, and may also be affected by short stature and/or diabetes. The invention also encompasses treatment of subjects diagnosed with visceral obesity, but who are not IGF-I deficient, diabetic, or affected by short stature.

An IGF-I deficient subject has levels of IGF-I below normal range for their age. IGF-I deficient subjects will generally have levels of IGF-I greater than −1 SD below normal, or greater than −2 SD below normal. An IGF-I deficient subject may also have Growth Hormorie Binding Protein less than normal or more than −2 SD below normal. An IGF-I deficient subject may also have a lower than normal IGFBP-3 concentration in blood.

IGF-I deficient subjects who will benefit from increased IGF-I levels can be identified using routine methods known in the art. IGF-I levels can be detected in blood. A genetic abnormality associated with IGF-I can be detected using standard genetic assays. A marker for a local IGF-I deficit (such as levels of IGFBP-1) can be detected using routine assays.

Measuring IGF levels in a biological fluid such as a body or blood fluid can be done by any means, including RIA and ELISA. For example, total IGF-I in the blood can be determined by commercially available radioimmunoassays (Medgenix Diagnostics, Brussels, Belgium; IGF-I RIA Kit, Nichols Institute, San Juan Capistrano, Calif.) especially after the extraction of the blood sample using acid ethanol to remove binding proteins which interfere with the detection of the IGF-I by competing with anti-IGF-I antibody. IGFBP can be measured using commercially available immunoradiometric assays (IRMAs) for measuring IGFBP-1 and IGFBP-3 (Diagnostic System Laboratories Inc., Webster, Tex.).

Another method involves measuring the level of "free" or active IGF in blood. For example, one method is described in U.S. Pat. No. 5,198,340, herein expressly incorporated by reference in its entirety. An additional method is described in U.S. Pat. No. 6,251,865, issued Jun. 26, 2001, herein expressly incorporated by reference in its entirety, for detecting endogenous or exogenous IGF bound to an IGF binding protein or the amount of a compound that binds to an IGF binding protein and does not bind to a human IGF receptor bound to an IGF binding protein or detecting the level of unbound IGF in a biological fluid. This method comprises: contacting the fluid with 1) a means for detecting the compound that is specific for the compound (such as a first antibody specific for epitopes on the compound) attached to a solid-phase carrier, such that in the presence of the compound the IGF binding sites remain available on the compound for binding to the IGF binding protein, thereby forming a complex between the means and the IGF binding protein; and 2) the compound for a period of time sufficient to saturate all available IGF binding sites on the IGF binding protein, thereby forming a saturated complex; contacting the saturated complex with a detectably labeled second means which is specific for the IGF binding protein (such as a second antibody specific for epitopes on the IGFBP) which are available for binding when the compound is bound to the IGF binding protein; and quantitatively analyzing the amount of the labeled means bound as a measure of the IGFBP in the biological fluid, and therefore as a measure of the amount of bound compound and IGF binding protein, bound IGF and IGF binding protein, or active IGF present in the fluid.

U.S. Pat. Nos. 5,593,844 and 5,210,017, herein expressly incorporated by reference in their entireties, disclose a ligand-mediated immunofunctional binding protein assay method that can be used to quantitate the amount of IGFBP in a liquid sample by the use of antibodies, where complex formation takes place between one of these binding proteins and the ligand that binds to it.

The quantitative technique mentioned above using antibodies, called the ligand-mediated immunofunctional method (LIFA), is described for determining the amount of IGFBP by contact with IGF in U.S. Pat. No. 5,593,844, herein expressly incorporated by reference in its entirety.

Normal subjects, i.e., those not displaying low IGF-I levels, obesity or symptoms of diabetes, who may be amenable to the methods and compositions of the invention can be identified by any method for predicting obesity, diabetes or diseases or conditions associated with IGF-I levels, including, but not limited to, genetic tests and screening of family histories.

Dosage and Schedule of Administration

Selection of the therapeutically or cosmetically effective dose can be determined (e.g., via clinical trials) by a skilled artisan, such as clinician or a physician, based upon the consideration of several factors which will be known to one of ordinary skill in the art. Such factors include, for example, the particular form of the compound which increases IGF-I serum levels, the compound's pharmacokinetic parameters such as bioavailability, metabolism, half-life, and the like, which are established during the development procedures typically employed in obtaining regulatory approval of a pharmaceutical compound. Further factors in considering the dose include the disease or condition to be treated, the benefit to be achieved in a subject, the subject's body mass, the subject's immune status, the route of administration, whether administration of the compound or combination therapeutic agent is acute or chronic, concomitant medications, and other factors known by the skilled artisan to affect the efficacy of administered pharmaceutical agents.

In some embodiments, the total pharmaceutically effective amount of IGF-I administered parenterally per dose will be in the range of about 5 μg/kg/day to about 400 μg/kg/day, including about 10 to about 80 μg/kg/day, such as about 20 to about 40 μg/kg/day, of subject body weight, although, this will be subject to a great deal of therapeutic discretion. The IGF-I may be administered by any means, including injections (single or multiple, e.g., 1-5 per day, including 2-4 per day) or infusions. In some embodiments, the IGF-I is administered once or twice per day by subcutaneous injection. If a slow release formulation is used, typically the dosages used (calculated on a daily basis) will be less, up to one-half of those described above.

In further embodiments of the invention, to reduce visceral fat (e.g., as assessed by the ratio of visceral fat to subcutaneous fat), IGF-I is administered at a dosage of about 20 to about 60 μg/kg/day, including about 30 to about 50 μg/kg/day, such as about 40 μg/kg/day.

The present invention further provides for a pharmaceutical composition that comprises a compound which increases IGF-I levels, and a pharmaceutically acceptable carrier. Suitable pharmaceutically acceptable carriers include essentially chemically inert and nontoxic pharmaceutical compositions that do not interfere with the effectiveness of the biological activity of the pharmaceutical composition. Examples of suitable pharmaceutical carriers include, but are not limited to, saline solutions, glycerol solutions, ethanol, N-(1(2,3-dioleyloxy)propyl)-N,N,N-trimethylammonium chloride (DOTMA), diolesylphosphotidylethanolamine (DOPE), and liposomes. Such pharmaceutical compositions should contain a therapeutically effective amount of the compound, together with a suitable amount of carrier so as to provide the form for proper administration to the subject. The formulation should suit the mode of administration. For example, oral administration requires enteric coatings to protect the compounds of the invention from degradation within the gastrointestinal tract. In another example, the compounds of the invention may be administered in a liposomal formulation, particularly for nucleic acids, to shield the compounds from degradative enzymes, facilitate transport in circulatory system, and effect delivery across cell membranes to intracellular sites.

In another embodiment, a pharmaceutical composition comprises a IGF-I protein, and/or one or more therapeutic agents; and a pharmaceutically acceptable carrier. In one embodiment, a pharmaceutical composition, comprising a IGF-I protein, with or without other therapeutic agents; and a pharmaceutically acceptable carrier, is at an effective dose.

The pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

In a preferred embodiment, the composition is formulated in accordance with routine procedures as a pharmaceutical composition adapted for subcutaneous injection or intravenous administration to humans. Typically, pharmaceutical compositions for subcutaneous injection or intravenous administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water-free concentrate in a hermetically sealed container such as an ampule or sachette indicating the quantity of active agent. Where the composition is to be administered by infusion, it can be dispensed with an infusion bottle, bag, or other acceptable container, containing sterile pharmaceutical grade water, saline, or other acceptable diluents. Where the composition is administered by injection, an ampule of sterile water for injection or saline can be provided so that the ingredients may be mixed prior to administration.

In some embodiments the formulation for IGF-I is that described in U.S. Pat. No. 5,681,814. This formulation is as follows: about 2 mg/ml to about 20 mg/ml of IGF-I, about 2 to about 50 mg/ml of an osmolyte, about 1 to about 15 mg/ml of at least one stabilizer, and a buffer (such as an acetic acid salt buffer, or sodium acetate) in an amount such that the composition has a pH of about 5 to about 5.5. Optionally, the formulation may also contain a surfactant, for example, in an amount of about 1-5 mg/ml, such as about 1 to about 3 mg/ml.

In some embodiments, the osmolyte is an inorganic salt at a concentration of about 2-10 mg/ml or a sugar alcohol at a concentration of about 40 to about 50 mg/ml, the stabilizer is benzyl alcohol, phenol, or both, and the buffered solution is an acetic acid salt buffered solution. In further embodiments, the osmolyte is an inorganic salt, such as sodium chloride.

In yet further embodiments, the formulation, the amount of IGF-I is about 8 to about 12 mg/ml, the amount of sodium chloride is about 5 to about 6 mg/ml, the stabilizers are benzyl alcohol in an amount of about 8 to about 10 mg/ml and/or phenol in an amount of about 2 to about 3 mg/ml, and the buffer is about 50 mM sodium acetate so that the pH is about 5.4. Optionally, the formulation contains polysorbate as a surfactant in an amount of about 1 to about 3 mg/ml.

Pharmaceutical compositions adapted for oral administration may be provided, for example, as capsules or tablets; as powders or granules; as solutions, syrups or suspensions (in aqueous or non-aqueous liquids); as edible foams or whips; or as emulsions. Tablets or hard gelatine capsules may comprise, for example, lactose, starch or derivatives thereof, magnesium stearate, sodium saccharine, cellulose, magnesium carbonate, stearic acid or salts thereof. Soft gelatine capsules may comprise, for example, vegetable oils, waxes, fats, semisolid, or liquid polyols, etc. Solutions and syrups may comprise, for example, water, polyols and sugars.

An active agent intended for oral administration may be coated with or admixed with a material (e.g., glyceryl monostearate or glyceryl distearate) that delays disintegration or affects absorption of the active agent in the gastrointestinal tract. Thus, for example, the sustained release of an active agent may be achieved over many hours and, if necessary, the active agent can be protected from being degraded within the gastrointestinal tract. Taking advantage of the various pH and enzymatic conditions along the gastrointestinal tract, pharmaceutical compositions for oral administration may be formulated to facilitate release of an active agent at a particular gastrointestinal location.

Pharmaceutical compositions adapted for parenteral administration include, but are not limited to, aqueous and non-aqueous sterile injectable solutions or suspensions, which may contain antioxidants, buffers, bacteriostats and solutes that render the pharmaceutical compositions substantially isotonic with the blood of an intended recipient. Other components that may be present in such pharmnaceutical compositions include water, alcohols, polyols, glycerine and vegetable oils, for example. Compositions adapted for parenteral administration may be presented in unit-dose or multi-dose containers, for example, sealed ampules and vials, and may be stored in a freeze-dried (lyophilized) condition requiring the addition of a sterile liquid carrier, e.g., sterile saline solution for injections, immediately prior to use. Extemporaneous injection solutions and suspensions may be prepared from sterile powders, granules and tablets. Such pharmaceutical compositions should contain a therapeutically or cosmetically effective amount of a compound which increases IGF-I serum levels, together with a suitable amount of carrier so as to provide the form for proper administration to the subject. The formulation should suit the mode of administration.

Pharmaceutical compositions adapted for transdermal administration may be provided as discrete patches intended to remain in intimate contact with the epidermis for a prolonged period of time. Pharmaceutical compositions adapted for topical administration may be provided as, for example, ointments, creams, suspensions, lotions, powders, solutions, pastes, gels, sprays, aerosols or oils. A topical ointment or cream is preferably used for topical administration to the skin, mouth, eye or other external tissues. When formulated in an ointment, the active ingredient may be employed with either a paraffinic or a water-miscible ointment base. Alternatively, the active ingredient may be formulated in a cream with an oil-in-water base or a water-in-oil base.

Pharmaceutical compositions adapted for topical administration to the eye include, for example, eye drops or injectable pharmaceutical compositions. In these pharmaceutical compositions, the active ingredient can be dissolved or suspended in a suitable carrier, which includes, for example, an aqueous solvent with or without carboxymethylcellulose. Pharmaceutical compositions adapted for topical administration in the mouth include, for example, lozenges, pastilles and mouthwashes.

Pharmaceutical compositions adapted for nasal administration may comprise solid carriers such as powders (preferably having a particle size in the range of 20 to 500 microns). Powders can be administered in the manner in which snuff is taken, i.e., by rapid inhalation through the nose from a container of powder held close to the nose. Alternatively, pharmaceutical compositions adopted for nasal administration may comprise liquid carriers such as, for example, nasal sprays or nasal drops. These pharmaceutical compositions may comprise aqueous or oil solutions of the active ingredient. Compositions for administration by inhalation may be supplied in specially adapted devices including, but not limited to, pressurized aerosols, nebulizers or insufflators, which can be constructed so as to provide predetermined dosages of the active ingredient.

Pharmaceutical compositions adapted for rectal administration may be provided as suppositories or enemas. Pharmaceutical compositions adapted for vaginal administration may be provided, for example, as pessaries, tampons, creams, gels, pastes, foams or spray formulations.

Suppositories generally contain active ingredients in the range of 0.5% to 10% by weight. Oral formulations preferably contain 10% to 95% active ingredient by weight.

In yet another embodiment, IGF-I may be administered using long-acting IGF-I formulations that either delay the clearance of IGF-I from the site or cause a slow release of IGF-I from, e.g., an injection or administration site. The long-acting formulation that prolongs IGF-I plasma clearance may be in the form of IGF-I complexed, or covalently conjugated (by reversible or irreversible bonding) to a macromolecule such as a water-soluble polymer selected from PEG and polypropylene glycol homopolymers and polyoxyethylene polyols, i.e., those that are soluble in water at room temperature. Alternatively, the IGF-I may be complexed or bound to a polymer to increase its circulatory half-life. Examples of polyethylene polyols and polyoxyethylene polyols useful for this purpose include polyoxyethylene glycerol, polyethylene glycol, polyoxyethylene sorbitol, polyoxyethylene glucose, or the like. The glycerol backbone of polyoxyethyiene glycerol is the same backbone occurring in, for example, animals and humans in mono-, di-, and triglycerides. The polymer need not have any particular molecular weight, but it is preferred that the molecular weight be between about 3500 and 100,000, more preferably between 5000 and 40,000. Preferably the PEG homopolymer is unsubstituted, but it may also be substituted at one end with an alkyl group. Preferably, the alkyl group is a C1-C4 alkyl group, and most preferably a methyl group. Most preferably, the polymer is an unsubstituted homopolymer of PEG, a monomethyl-substituted homopolymer of PEG (mPEG), or polyoxyethylene glycerol (POG) and has a molecular weight of about 5000 to 40,000.

Administration of the pharmaceutical compositions of the invention includes, but is not limited to, oral, intravenous infusion, subcutaneous injection, intramuscular, topical, depo injection, implantation, time-release mode, intracavitary, intranasal, inhalation, intratumor, intraocular, and controlled release. The pharmaceutical compositions of the invention also may be introduced parenterally, transmucosally (e.g., orally), nasally, rectally, intravaginally, sublingually, submucosally, or transdermally. Preferably, administration is parenteral, i.e., not through the alimentary canal but rather through some other route via, for example, intravenous, subcutaneous, intramuscular, intraperitoneal, intraorbital, intracapsular, intraspinal, intrasternal, intra-arterial, or intradermal administration. The skilled artisan can appreciate the specific advantages and disadvantages to be considered in choosing a mode of administration. Multiple modes of administration are encompassed by the invention. For example, a IGF-I protein is administered by subcutaneous injection, whereas a combination therapeutic agent is administered by intravenous infusion. Moreover, administration of one or more species of IGF-I proteins, with or without other therapeutic agents, may occur simultaneously (i.e., co-administration) or sequentially. For example, a IGF-I protein is first administered to increase sensitivity to subsequent administration of a second therapeutic agent or therapy. In another embodiment, the periods of administration of one or more species of IGF-I protein, with or without other therapeutic agents may overlap. For example, a IGF-I protein is administered for 7 days, and a second therapeutic agent is introduced beginning on the fifth day of IGF-I protein treatment, and treatment with the second therapeutic agent continues beyond the 7-day IGF-I protein treatment. The IGF-I can also be administered intermittently in a cyclical manner as described in U.S. Pat. No. 5,565,428.

In one embodiment, a pharmaceutical composition of the invention is delivered by a controlled-release or sustained release system. For example, the pharmaceutical composition may be administered using intravenous infusion, an implantable osmotic pump, a transdermal patch, liposomes, or other modes of administration. In one embodiment, a pump may be used (See, e.g., Langer, 1990, Science 249:1527-33; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, the compound can be delivered in a vesicle, in particular a liposome (See, e.g., Langer, Science 249:1527-33 (1990); Treat et al., 1989, in *Liposomes in the Therapy of Infectious Disease and Cancer*, Lopez-Berestein and Fidler (eds.), Liss, New York, pp. 353-65; Lopez-Berestein, ibid., pp. 317-27 International Patent Publication No. WO 91/04014; U.S. Pat. No. 4,704,355). In another embodiment, polymeric materials can be used (See, e.g., *Medical Applications of Controlled Release*, Langer and Wise (eds.), CRC Press: Boca Raton, Fla., 1974; *Controlled Drug Bioavailability, Drug Product Design and Performance*, Smolen and Ball (eds.), Wiley: New York (1984); Ranger and Peppas, 1953, J. Macromol. Sci. Rev. Macromol. Chem. 23:61; Levy et al., 1985, Science 228:190; During et al., 1989, Ann. Neurol. 25:351; Howard et al., 1989, J. Neurosurg. 71:105). Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (see Sidman et al., 1983, Biopolymers, 22:547-556), poly(2-hydroxyethyl methacrylate) (Langer et al., 1981, J. Biomed Mater Res, 15:167-277), and Langer, 1982, Chem Tech, 12:98-105), ethylene vinyl acetate (Langer et al., supra) or poly-D-(−)-3-hydroxybutyric acid (EP 133,988). Sustained-release IGF-I compositions also include liposomally entrapped IGF-I. Liposomes containing IGF-I are prepared by methods known per se: DE 3,218,121; Epstein et al., 1985, Proc Natl Acad Sci USA, 82:3688-3692; Hwang et al, 1980, Proc Natl Acad Sci USA, 77: 4030-4034; EP 52,322; EP 36,676; EP 88,046; EP 143,949; EP 142,641; Japanese Pat. Appln. 83-118008; U.S. Pat. Nos. 4,485,045 and 4,544,545; and EP 102,324. Ordinarily, the liposomes are of the small (from or about 200 to 800 Angstroms) unilamellar type in which the lipid content is greater than about 30 mol percent cholesterol, the selected proportion being adjusted for the optimal IGF-I therapy.

In yet another embodiment, a controlled release system can be placed in proximity of the target. For example, a micropump may deliver controlled doses directly into the brain, thereby requiring only a fraction of the systemic dose (See, e.g., Goodson, 1984, in *Medical Applications of Controlled Release*, vol. 2, pp. 115-138). IGF-I could be delivered directly into the peritoneal cavity to preferentially expose visceral fat to drug.

In one embodiment, it may be desirable to administer the pharmaceutical composition of the invention locally to the area in need of treatment; this may be achieved, for example, and not by way of limitation, by local infusion during surgery, topical application (e.g., in conjunction with a wound dressing after surgery), injection, by means of a catheter, by means of a suppository, or by means of an implant. An implant can be of a porous, non-porous, or gelatinous material, including membranes, such as sialastic membranes, or fibers.

A compound which increases IGF-I levels can be administered before, during, and/or after the administration of one or more therapeutic agents. In yet another embodiment, there can be a period of overlap between the administration of IGF-I protein and/or one or more therapeutic agents.

The present invention may be better understood by reference to the following non-limiting Examples, which are provided only as exemplary of the invention. The following examples are presented to more fully illustrate the embodiments of the invention. They should in no way be construed, however, as limiting the broader scope of the invention.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The following methods and materials are used in the examples below.

Study Design

Most individuals with Type II diabetes mellitus (DM) who have initially been treated with diet and exercise will later require an oral hypoglycemic drug for glucose control. After 10 years, 50% of individuals initially responding to an oral agent will fail to achieve satisfactory glycemic control and will ultimately require insulin therapy. See Yki-Järvinen H et al., 1992, N Engl J Med 327:1426-33. Short-term insulin therapy is associated with an average weight gain of 5 to 6 kg, two-thirds of which is attributable to an increase in fat mass over the long term. See Koivisto V A., 1993, Diabetes Care 16 Suppl 3:29-39.

Accordingly, subjects with type II DM were treated with a combination of rhIGF-I and glyburide, or with rhIGF-I or glyburide alone, to ascertain the potential benefits of the addition of rh1GF-I to glyburide therapy on glycemic control, incidence of hypoglycemia, and weight gain.

A double-blind, randomized, placebo-controlled study was designed to evaluate the safety and pharmacokinetic and pharmacodynamic effects of rhIGF-1. rhIGF-I or rhIGF-I placebo (20 microgram/kg BID or 40 microgram/kg BID) was administered subcutaneously in addition to oral (PO) glyburide or glyburide placebo. The use of any additional orally administered drug or insulin to treat hyperglycemia during the pretreatment and treatment periods was prohibited.

The study consisted of four phases: 1) a 2-week screening period, 2) a 4-week pretreatment period (day 28 through day 1), 3) a 12-week treatment period (day 1 through week 12), and 4) a 2-week post-treatment period (week 12 through week 14 or 2 weeks following completion of an early termination visit).

Description and Rational for the Study

The efficacy endpoints were the change in glucose control as assessed by the change from baseline (day 1 to week 12) in hemoglobin A1c (HbA1c) levels, and changes from baseline (day 1 to week 12) in fasting blood glucose (BG), body weight, and visceral and mid-thigh fat.

All adverse events occurring during the treatment and post-treatment periods of the study (day 1 to week 14) were monitored through the follow-up evaluation at week 14. Adverse events continuing beyond the follow-up period were monitored until resolution, as appropriate.

Safety Plan

Based on clinical studies with doses of rhIGF-I in the range used in this study, the most common expected adverse events included jaw pain, edema, arthralgias, and myalgias. When these events occurred, they generally did not require discontinuation of rhIGF-I at the doses used in this study. The edema tended to be cosmetic and generally resolved without additional treatment. Occasionally, treatment with a mild diuretic was necessary.

Because concern existed regarding the effects of rhIGF-I on two types of ocular findings—progression of diabetic retinopathy and optic disc swelling—the occurrence of such findings was recorded as a measure of safety. An ophthalmologic visit for dilated funduscopic examination was performed during the screening period. Additionally, fundus photography was performed on each subject prior to initiation of treatment with rhIGF-I or placebo between day 7 and day 1. When optic disc swelling was detected on the initial baseline photograph, the subject was terminated from the study immediately. If the baseline photograph was scored at an Early Treatment Diabetic Retinopathy Study (ETDRS) scale of greater than 35 in either eye, the subject was also not allowed to progress further in the study.

Both the ophthalmologic examination and fundus photography were repeated at the completion of the treatment period or at the early termination visit in the event of premature termination. The ophthalmologic exam was performed within 3 days of the fundus photography. In the event that optic disc swelling was detected on the fundus photograph obtained at the week 12 or early termination visits, subjects were asked to return for repeat fundus photography at 1-3 months following discontinuation from the study, and again at 3-month intervals until the optic disc swelling resolved.

Fundus photographs, obtained for each subject at week 12 or at the early termination visit, were compared with the photographs obtained prior to treatment in order to evaluate the development of retinopathy during the course of the study. The photographs for each eye were graded using the final version of the ETDRS scale. The resulting scores for each eye were combined to yield the ETDRS person score. A change between day 1 and week 12 (or early termination) in the full scale ETDRS person score of three or more levels (5 units) was recorded as a progression of retinopathy and as an adverse event. For example, if a subject had a baseline score of 20/20 and then at Week 12 a score of 35/35, three steps of 5 units, the change was recorded as an adverse event.

In addition to the adverse events described above, hypoglycemia was expected to occur in some subjects. Hypoglycemia was defined as a BG of <50 mg/dL as indicated by the One-Touch Profile BG meter or the clinical laboratory. In the event of repeated hypoglycemic episodes, the glyburide dose could be decreased (during the treatment period only). Symptomatic hypoglycemic episodes, regardless of blood glucose reading, were documented as hypoglycemia.

Subjects

This study aimed to include ~200 men and women (a minimum of 85 subjects of each gender) with type II DM who were currently treated for hyperglycemia with oral medication(s) only.

Formulations rhIGF-I was provided by Genentech, Inc. in a vial containing a sterile, benzyl alcohol-preserved solution of 70 mg of rhIGF-I in 7 mL of acetate/NaCl, pH 5.4

Glyburide tablets (Diabeta, 5-mg tablets manufactured by Hoechst) were obtained commercially and encapsulated intact in opaque gelatin capsules. The glyburide placebo tablets contained the product excipients without active ingredient. The glyburide placebo tablet was physically similar to the active tablet and was encapsulated intact in identical opaque gelatin capsules.

Subjects were asked to discontinue their current oral hypoglycemic agent dosing and begin taking open-label glyburide (10 mg PO BID/two 5-mg capsules BID) at Day –28 for the 4-week treatment period.

Treatment Groups and Dosing Regimens

Subjects were randomized to receive one of the five following regimens (about 40 per group) during the 12-week treatment period as shown in Table 1. Randomization was stratified by gender, by prior oral hyperglycemic agent therapy, and by HbA1c level at day 14.

The sample size was intended to be 40 subjects per treatment group for a total of 200 subjects. Based on an estimated standard deviation of 1.2% for change in HbA1c, the study was estimated to have a 90% power to detect a difference of 1% in group means for this endpoint.

TABLE 1

Treatment Groups and Dosing Regimens

| | Treatment Group | Regimen |
|---|---|---|
| 1 | rhIGF-I placebo | and glyburide 10 mg BID |
| 2 | rhIGF-I 20 µg/kg BID | and glyburide 10 mg BID |
| 3 | rhIGF-I 40 µg/kg BID | and glyburide 10 mg BID |
| 4 | rhIGF-I 20 µg/kg BID | and glyburide placebo |
| 5 | rhIGF-I 40 µg/kg BID | and glyburide placebo |

All rhIGF-I (active or placebo) dose calculations were based on total body weight at day –14. The rhIGF-I placebo were injected into the SC tissue.

Statistical Efficacy Analysis

The primary efficacy variable for the assessment of treatment effect on glucose control at Week 12 was the change from baseline (day 1) in HbA1c levels. Secondary efficacy variables assessing glucose control at Week 12 were the change from baseline (day 1) for each of the following: fasting blood glucose concentration, weight, and visceral and mid-thigh fat.

Computer Tomography (CT) Scan Measurement of Body Fat

All CT scans were performed on GE Sytec 4000 CT scanners or an equivalent scanner.

Mid-Thigh CT Scan

An initial Thigh Scan was performed using the following procedure:
1. The subject lay on the CT bed with his or her feet toward the scanner. The subject's knees were at least 3 inches above the extended bed joint, not over the joint.
2. The legs were positioned so they were not touching each other and the hands were crossed over the abdomen so as not to interfere with the scan.
3. The CT technician then positioned the bed. The entire femur was visualized in the initial topogram.
4. The technician then made a topogram of the entire femur of the non-dominant leg and recorded this picture on the film. The length of the femur was then measured and recorded and this measurement was used to identify the midpoint of the femur. This midpoint was used to assess the cross section of the thigh.

5. The technician took a 10-mm slice at the precise level of the mid-point of the femur with the following settings for a GE Sytec 4000 scanner:
   kV=100
   MA=170
   1 sec
   DFOV=21
   Algorithm=standard Technicians were advised that although settings for some scanners may be slightly different, the settings must be standardized so as to give the greatest definition for fat and lean tissue. Once the technician determined the appropriate setting for a scanner, he or she was advised to use the same settings for every (slice) scan. The topograms could be at different settings as the topograms would not be imaged.

6. The entire cross section of the nondominant thigh was visualized on the screen. If the entire thigh was not visualized on the screen, the picture was reconfigured with a larger display field of view. Once the entire thigh was visualized on the screen, the technician downloaded the cross section to the disk. The disk was checked to make sure the image was actually there, and then the picture was recorded on film.

7. The exam number, series number, and image number of the slice was then recorded.

8. The technician sent the film to the printer at this point. The film was set at four pictures per film, and the film had for the femur the recorded total distance, the midpoint, and the slice of the thigh.

The same leg (left) was used as in the initial scan. A topogram of the thigh was taken, and a measurement made down the femur to the midpoint of the femur using the same distance as was used in the baseline thigh scan. A 10-mm cross section scan was taken at the midpoint using the identical settings as were used for the baseline scan. A record was made of the exam number, series number, and image number of the slice.

Abdominal CT Scan

An initial Abdominal Scan was performed using the following procedure:

1. After the thigh scan was complete, a small triangular wedge pillow was placed under the subject's knees to help tilt the spine to the correct position. The arms were crossed over the chest/neck with elbows up and out of the way of the abdomen. The subject's underpants were pulled down so that the elastic of the underwear was well out of the way of the site where the scan was taken.

2. The technician positioned the bed in the scanner so that a lateral topogram could be taken that included at least T12 through L5 of the spine. This picture was recorded on film.

3. The location of the midsection of L3 was identified.

4. A 10-mm slice at the level of the midpoint of L3 (angle must be zero so that the slice was perpendicular) was taken at the same settings as were used for the thigh slice, with the exception of the DFOV, which was 35 or 45 (35 for a small person and 45 for a large person).

The entire cross section of the abdomen was on the screen. If the entire abdomen was not on the screen, the picture was reconfigured. Once the entire abdomen was on the screen, the technician downloaded it onto the disk and verified that the image was actually on the disk. This was then recorded on film.

5. The technician sent the film to the printer at this point. It was a requirement that each film had four pictures, and the film had the lateral topogram of the spine and the slice.

6. The technician then recorded the exam number, the series number, and the image number of slice.

7. The subject was then removed from the table if there were no more measurements to obtain and the film was collected.

The same procedures were then followed for the repeat abdominal scans with identical settings and locations being used for the repeat scans.

It was a requirement that the films should contain the following information:
Thigh
Topogram of entire thigh
Topogram with the femur distance measured (both the entire distance and the distance with the midpoint drawn)
Entire thigh cross section
Trunk
Lateral spine with identification of the midpoint of L3
Entire slice at the level of L3
The disks contained the following information:
Cross section of the thigh
Cross section of the trunk at L3
Data Management Slices were downloaded onto the scanner and then retrieved via optical disk (or the Internet if possible) to a computer for analysis. During analysis, the area of intra-abdominal and subcutaneous fat as well as oblique, psoas, quadratum laborum, and sacrospinalis muscles were measured. The images were digitized by optical density to separate bone, muscle, and fat compartments using a modified version of the NIH IMAGE program. Pixel units were converted to area measurements using an internal calibration standard. Digitized images were analyzed in a blinded fashion. The coefficient of variation of repeated analysis of a single scan is <1.5%.

Example 1

Treatment Effect on Glucose Control

The primary efficacy variable for the assessment of treatment effect on glucose control was the change from baseline (day 1) in HbA1c levels. The results are shown in Table 2. The high basal HbA1c values show that at baseline the patients could be characterized as being poorly controlled Type II diabetics. Inspection of Table 2 shows that there was a maintained and progressive beneficial effect of treatment with IGF-1 on HbA1c.

The intent to treat analysis is shown in the last column of Table 2 as the "Endpoint Change %" or the last available measurement carried forward. This measure of efficacy was statistically significant for both combination groups compared to baseline ($p<0.0001$) and for the high dose IGF-1 alone ($p=0.038$). In addition compared to glyburide alone the combination treatments (both high and low doses) also significantly reduced HbA1c ($p<0.0001$) and high dose IGF-1 alone also reduced HbA1c compared to glyburide alone ($p=0.043$).

The magnitude of the falls in HbA1c was very large. The high dose of IGF-1 when given in combination with glyburide at week 12 reduced HbA1c by 1.75% and the low dose by 1.22%, while the glyburide treated group who did not receive IGF-1 increased their HbA1c by 0.32%. Therefore the difference between the glyburide alone group and the two combination treated groups at week 12 was for the high dose group −2.0%, and for the low dose IGF-1 −1.5%. These are very large decreases in HbA1c and were highly statistically significant ($p<0.0001$ vs baseline and $p<0.0001$ vs glyburide alone). Therefore, IGF-I was especially efficacious when combined with the insulin secretagogue, glyburide.

In addition, IGF-1 alone reduced HbA1c. At week 12 the high dose of IGF-1 reduced HbA1c by −0.58%, which was a statistically significant change ($p=0.035$). It should be noted that this decrease occurred despite the patients previous treatment, glyburide being withdrawn. Therefore, the results show that, in terms of its effect on HbA1c, IGF-1 is a superior treatment to an established therapy, glyburide.

TABLE 2

Mean (SD) Hemoglobin $A_{1c}$ (%): Baseline and Change from Baseline

| Treatment Group | Baseline % | Week 4 Change % | Week 8 Change % | Week 12 Change % | Endpoint[b] Change % |
|---|---|---|---|---|---|
| IGF-I Placebo (Glyburide Active) N = 19 | 9.46 (1.2) | −0.13 (0.5) | 0.05 (0.7) | 0.32 (0.7) | 0.12 (0.8) |
| 20 μg/kg IGF-I (Glyburide Active) N = 19 | 9.94 (1.5) | −0.81 (0.7) | −1.22 (0.9) | −1.22 (1.0) | −0.87 (0.9) |
| 40 μg/kg IGF-I (Glyburide Active) N = 19 | 9.47 (1.2) | −0.93 (0.6) | −1.45 (0.8) | −1.75 (0.9) | −1.32 (0.9) |
| 20 μg/kg IGF-I (Glyburide Placebo) N = 16 | 9.93 (1.4) | −0.10 (0.6) | −0.29 (0.8) | 0.13 (1.2) | 0.04 (0.9) |
| 40 μg/kg IGF-I (Glyburide Placebo) N = 14 | 9.79 (1.2) | −0.37 (0.5) | −0.47 (0.9) | −0.58 (1.2) | −0.30 (0.8) |

[b]For subjects missing Week 12 values for HbA1c, the endpoint was the last available measurement carried forward for analysis.

Example 2

Safety of IGF-I Treatment

The safety of IGF-I treatment in combination with glyburide is demonstrated in Tables 3 and 4. As shown in Table 3, at the doses of IGF-I used, there was a low incidence of side effects. Table 4 shows the ETDRS scores for the retinas of the subjects in the 5 treatment groups. It is clear that treatment with IGF-I did not cause a progression of retinopathy (increases in the ETDRS scores).

Moreover, treatment with IGF-I resulted in improvements in retinopathy (decreases in the ETDRS scores). Only one subject in the Placebo/glyburide group (the only group not treated with IGF-I) showed an improvement in retinal score, whereas in each of the groups treated with IGF-I, 4, 4, 6, and 5 subjects (IGF-I 20+Glyburide, IGF-I 40+Glyburide, IGF 20+Placebo, and IGF-I 40+Placebo, respectively) showed an improvement in their retinal scores. The results show that IGF-I can improve glucose control (lower hemoglobin A1c) and reduce visceral obesity while likely improving retinal scores in diabetic subjects.

TABLE 3

Most Frequently (>5%) Reported Adverse Events Judged to Be Possibly or Probably Related to Study Drug, n (%)

| Preferred Term | Pla + Gly (N = 34) | IGF-I 20 + Gly (N = 39) | IGF-I 40 + Gly (N = 39) | IGF-I 20 + Pla (N = 38) | IGF-I 40 + Pla (N = 36) | Total (N = 186) |
|---|---|---|---|---|---|---|
| Pain | 2 (6) | 4 (10) | 8 (21) | 6 (16) | 6 (17) | 26 (14) |
| Hypoglycemia | 3 (9) | 7 (18) | 10 (26) | 2 (5) | 1 (3) | 23 (12) |
| Headache | 2 (6) | 4 (10) | 7 (18) | 3 (8) | 6 (17) | 22 (12) |
| Peripheral Edema | 0 | 5 (13) | 7 (18) | 1 (3) | 9 (25) | 22 (12) |
| Jaw pain | 1 (3) | 3 (8) | 5 (13) | 2 (5) | 7 (19) | 18 (10) |
| Arthralgia | 1 (3) | 5 (13) | 2 (5) | 1 (3) | 3 (8) | 12 (6) |
| Asthenia | 2 (6) | 3 (8) | 0 | 3 (8) | 3 (8) | 11 (6) |

TABLE 4

ETDRS - an integrated score of the health of the retina
Change in EDTRS Levels, n (%)

|  | Pla + Gly (N = 34) | IGF-I 20 + Gly (N = 39) | IGF-I 40 + Gly (N = 39) | IGF-I 20 + Pla (N = 38) | IGF-I 40 + Pla (N = 36) | Total (N = 186) |
|---|---|---|---|---|---|---|
| n | 29 | 36 | 36 | 35 | 33 | 169 |
| −1- to −2-step progression | 1 (3) | 4 (11) | 4 (11) | 6 (17) | 5 (15) | 20 (12) |
| No change | 19 (66) | 22 (61) | 24 (67) | 24 (69) | 20 (61) | 109 (65) |
| 1- to 2-step Progression | 8 (28) | 9 (25) | 7 (19) | 4 (11) | 7 (21) | 35 (21) |
| ≧3-step progression | 1 (3) | 1 (3) | 1 (3) | 1 (3) | 0 | 4 (2) |

A change in ETDRS level was the maximum difference between baseline and on-study or post-treatment values. A negative change indicated improvement.

Example 3

Change in Body Weight and BMI in Response to Treatment

Secondary efficacy variables assessing glucose control at Week 12 were the change from baseline (Day 1) for each of the following: weight, and visceral and mid-thigh fat. Table 5 shows the change in weight and the standard error of the mean (SE) in each treatment group.

TABLE 5

Body Weights and Changes from Day 1 to Weeks 8, 12 and 14

| Treatment Group | Mean Weight (SE) Day 1 (kg) | Weight Change (SE) Week 8 (kg) | Weight Change (SE) Week 12 (kg) | Weight Change (SE) Week 14 (kg) |
|---|---|---|---|---|
| IGF-I Placebo (Glyburide Active) N = 19 | 94.3 (2.9) | −0.2 (0.4) | −0.1 (0.5) | 0.0 (0.8) |
| 20 μg/kg IGF-I (Glyburide Active) N = 19 | 101.2 (3.6) | 0.9 (0.4) | 0.1 (0.4) | −0.5 (0.7) |
| 40 μg/kg IGF-I (Glyburide Active) N = 19 | 96.0 (3.1) | 1.5 (0.4) | 1.8 (0.6) | 0.0 (0.7) |
| 20 μg/kg IGF-I (Glyburide Placebo) N = 16 | 95.1 (2.6) | −1.5 (0.6) | −2.8 (0.7) | −2.7 (0.6) |
| 40 μg/kg IGF-I (Glyburide Placebo) N = 14 | 102.1 (3.0) | −0.2 (0.5) | −0.6 (0.7) | −1.6 (0.5) |

The results show that during combination therapy there is a small weight gain, and treatment with IGF-I alone yields a weight loss while after treatment is stopped the weight loss caused by IGF-I alone is maintained but the small weight gain caused by combination treatment is reversed. The subjects treated with low dose IGF-I progressively lost weight during the study, on average they lost 1.5 kg at Week 8 and 2.8 kg at Week 12. This weight loss in the low dose group was maintained even 2 weeks after treatment with IGF-I was stopped when the weight loss was 2.7 kg (p=0.0069 vs Glyburide alone). A dose-related effect of treatment with IGF-I was observed as the 20 μg group showed more weight loss than the 40 μg IGF-I groups. Therefore, when given alone IGF-I can cause weight loss in Type II diabetic subjects. The combination of IGF-I plus glyburide increased weight at week 8 compared to treatment with IGF-I alone; this result was highly statistically significant at week 8 (P<0.0001) and week 12 (p<0.0001); however stopping treatment caused this weight to be lost so that at week 14 there was no difference between groups treated with glyburide alone or glyburide plus IGF-I. Overall glyburide reduced the weight loss caused by IGF-I. However it is significant that IGF-I could improve glucose control (reduce HbA1c) without causing a maintained increase in body weight. In contrast, IGF-I alone improved both HbA1c and reduced body weight, a very favorable combination of activities.

TABLE 6

BMI and Changes in BMI from Day 1 to Weeks 8, 12 and 14

| Treatment Group | BMI Baseline (SE) Day 1 (kg/m$^2$) | BMI Change (SE) Wk 8 (kg/m$^2$)) | BMI Change (SE) Wk 12 (kg/m$^2$) | BMI Change (SE) Wk 14 (kg/m$^2$) |
|---|---|---|---|---|
| IGF-I Placebo (Glyburide Active) N = 19 | 32.4 (0.8) | −0.1 (0.1) | 0.0 (0.2) | 0.0 (0.3) |
| 20 µg/kg IGF-I (Glyburide Active) N = 19 | 33.4 (0.8) | 0.3 (0.1) | 0.1 (0.1) | −0.2 (0.2) |
| 40 µg/kg IGF-I (Glyburide Active) N = 19 | 32.4 (0.9) | 0.5 (0.1) | 0.6 (0.2) | 0.0 (0.2) |
| 20 µg/kg IGF-I (Glyburide Placebo) N = 16 | 32.3 (0.8) | −0.5 (0.2) | −1.0 (0.2) | −0.9 (0.2) |
| 40 µg/kg IGF-I (Glyburide Placebo) N = 14 | 34.6 (0.8) | −0.1 (0.2) | −0.2 (0.2) | −0.6 (0.2) |

The degree of obesity in humans is commonly assessed by calculating the body mass index or BMI. The BMI is essentially correcting body weight for height. Obviously a very tall person will likely weigh more than a person with short stature so this correction for height makes BMI a better gauge of the degree of obesity than uncorrected body weight. Table 6 gives the BMI data for the subjects treated with IGF-I. At baseline the subjects had average BMIs of over 30. Overweight is defined as a BMI of over 25 and obesity is defined as a BMI of over 30. The BMI results show that the subjects who entered this study were almost all obese and many were morbidly obese. Treatment with IGF-I reduced BMI and this effect was maintained until week 14, which was 2 weeks after treatment with IGF-I was stopped. In subjects treated with 20 micrograms of IGF-I, BMI fell by 1.0 kg/m$^2$ at 12 weeks and 0.9 kg/m$^2$ at week 14. This effect of IGF-I on BMI was highly statistically significant versus glyburide at week 12 ($p=0.019$) and week 14 ($p=0.0064$). Therefore IGF-I had the ability to reduce BMI or directly affect the most widely accepted measure of obesity. There was a dose-related effect as high dose IGF-I at 40 micrograms/kg increased BMI when given in combination with glyburide, and had a lesser effect than the low dose of IGF-I when give alone. This greater effect of low dose IGF-I was unexpected.

Example 4

Change in Computer Tomography (CT) Scan Measurement of Body Fat in Response to Treatment Another independent measurement was that the CT scan assessed the abdominal diameter and the abdominal perimeter (e.g., belt size). The abdominal perimeter in subjects treated with glyburide alone was unchanged (−0.3±0.8 cm, mean±SEM) but in subjects treated with IGF-I at 20 micrograms/kg it was reduced (−1.4±0.8 cm) and was reduced even more in subjects treated with 40 micrograms/kg to (−2.9±1.3 cm). This reduction in "girth" caused by high dose IGF-I was, in layman's terms over an inch, or one belt notch, clearly a significant effect in only 12 weeks.

The body components contributing to these beneficial effects of IGF-I on body weight, BMI and girth were then analyzed by studying the changes in body composition as measured by computerized scanning. Two scans were performed. A scan was performed before treatment with IGF-I and another scan was performed after treatment with IGF-I. These two scans were analyzed by measuring the area of fat so that the effect of treatment with IGF-I could be ascertained.

The effect of IGF-I on body fat was estimated using the visceral adipose tissue (VAT) in abdomen and the subcutaneous adipose tissue (SAT) in the abdomen. The absolute changes in fat and the percent changes in fat were both analyzed. The percent changes were analyzed to guard against subjects with larger amounts of fat being given undue statistical weight in the analyses. The data for visceral adipose tissue (VAT) and subcutaneous adipose tissue (SAT), respectively are summarized in Table 7.

TABLE 7

Adipose Tissue by Abdominal CT Scans
(Means and (Standard Errors of Means))

| Group (n) | Change in VAT (cm$^2$) | Change in SAT (cm$^2$) | Mean VAT % Change | Mean SAT % Change |
|---|---|---|---|---|
| Placebo (Glyb. Active) (14) | 13.6 (6.4) | 2.0 (5.6) | 9.3 (3.9) | 1.0 (1.9) |
| IGF-I 20 µg/kg (Glyb. Active) (11) | −7.1 (4.8) | −1.7 (6.4) | −1.7 (2.3) | 0.1 (2.5) |
| IGF-I 40 µg/kg (Glyb. Active) (17) | −11.3 (9.4) | −3.0 (8.8) | −0.6 (4.3) | −1.7 (3.4) |
| IGF-I 20 µg/kg (Glyb. Plac.) (13) | 1.0 (9.0) | −12.3 (4.1) | 1.0 (4.0) | −6.0 (2.6) |
| IGF-I 40 µg/kg (Glyb. Plac.) (15) | −20.0 (7.6) | −16.1 (5.4) | −9.4 (3.9) | −6.4 (2.5) |

The data in Table 7 shows the changes in body fat measurements for the abdominal scans. The amounts of VAT and SAT measured by CAT scan are expressed in two ways, as either: 1) the absolute change from baseline (in square cm of fat) or 2) the percentage change in fat from baseline (% change). The percent change in VAT is also presented in FIG. 1.

Irrespective of how the amount of fat was expressed the data shows that in humans glyburide alone increased visceral fat (VAT) (for example, by 9%). In comparison there was little effect of glyburide on subcutaneous abdominal fat (it increased by 1%). When the combination of glyburide and IGF-I was administered, this increase in visceral fat was reversed when the measurements were expressed as either the change in the absolute amount (area) of fat or the percentage change in the amount of fat. Further, IGF-I alone at 40 µg/kg was able to reduce visceral fat area by almost 10%. Compared to glyburide treatment this effect of IGF-I alone on the percent visceral fat was statistically significant (p=0.021).

TABLE 8

Adipose Tissue by Thigh CT Scans
(Means and (Standard Errors of Means))

| Group (n) | Baseline TAT (sq cm) | Change in TAT (sq cm) | Change in TAT (%) |
|---|---|---|---|
| Placebo (Glyb. Active) (14) | 105.8 (9.6) | 1.0 (1.6) | 2.5 (2.0) |
| IGF-I 20 µg/kg (Glyb. Active) (12) | 103.3 (10.5) | 2.3 (2.7) | 2.4 (2.6) |
| IGF-I 40 µg/kg (Glyb. Active) (17) | 91.1 (7.4) | 1.4 (2.2) | 3.4 (2.7) |
| IGF-I 20 µg/kg (Glyb. Plac.) (13) | 89.2 (15.5) | −1.2 (2.8) | −1.4 (3.7) |
| IGF-I 40 µg/kg (Glyb. Plac.) (15) | 97.4 (9.5) | 0.3 (4.3) | 3.9 (4.3) |

The data in Table 8 shows the changes in body fat measurements for the thigh scans. The amount of thigh fat was measured by CAT scan, and Table 8 shows the data expressed as either: 1) the absolute amount at baseline of Thigh Adipose Tissue (TAT); 2) the absolute change from baseline in TAT (in square cm of fat); or 3) the percentage change from baseline in TAT (%).

Almost all the fat in the thigh was subcutaneous fat. Irrespective of how the amount of fat in the thigh was expressed the data shows that there was little change in thigh fat due to treatment. This data on subcutaneous thigh fat is in marked contrast to the data in Table 7 where visceral fat was reduced by almost 10% by treatment with IGF-I.

Thus, in addition to causing weight loss and a reduction in BMI in Type II diabetic subjects, the results show that IGF-I administration causes a redistribution of fat, such as, reducing the ratio of visceral fat to subcutaneous fat.

All references cited herein are specifically incorporated by reference as if fully set forth herein.

Having hereinabove disclosed exemplary embodiments of the present invention, those skilled in the art will recognize that this disclosure is only exemplary such that various alternatives, adaptations, and modifications are within the scope of the invention, and are contemplated by the Applicant. Accordingly, the present invention is not limited to the specific embodiments as illustrated above, but is defined by the following claims.

What is claimed:

1. A method for reducing visceral fat in a subject having an excess of visceral fat, the method comprising:
   a) diagnosing the subject as having an excess of visceral fat; and
   b) administering to the subject a compound that increases the bioactive serum levels of insulin-like growth factor-I (IGF-I) in an amount effective to reduce visceral fat in said subject, wherein the compound is not growth hormone.

2. The method of claim 1, wherein either (i) the subject is an adult human male and is type II diabetic and has a waist size of at least 40 inches before treatment with such compound or (ii) the subject is an adult human female and is type II diabetic and has a waist size of at least 35 inches before treatment with such compound.

3. The method of claim 2, wherein the reduction in visceral fat of the subject is assessed by determining the ratio of visceral fat to subcutaneous fat.

4. The method of claim 2, wherein the reduction in visceral fat of the subject is assessed by a decrease in a ratio of waist measurement to hip measurement of the subject.

5. The method of claim 2, wherein the reduction in visceral fat of the subject is assessed by computer tomography (CT) scan.

6. The method of claim 2, wherein the compound is IGF-I.

7. The method of claim 6, wherein the IGF-I is complexed with insulin-like growth factor binding protein-3 (IGFBP-3).

8. The method of claim 6, wherein the amount of IGF-I is greater than or equal to 40 µg/kg/day.

9. The method of claim 6, wherein said IGF-I is administered subcutaneously.

10. The method of claim 2, wherein the compound is administered with an effective amount of a growth-promoting agent.

11. The method of claim 10, wherein the growth-promoting agent is an insulin-like growth factor binding protein (IGFBP).

12. The method of claim 11, wherein the IGFBP is IGFBP-3.

13. The method of claim 10, wherein the compound is IGF-I.

14. The method of claim 1, wherein the subject is an adult human that presents, before treatment with such compound, a body composition characterized by a ratio of visceral fat to subcutaneous fat that is higher than the ratio of visceral fat to subcutaneous fat that characterizes the average body composition of normal adult humans of the same body mass index (BMI) and gender as the subject.

15. The method of claim 1, wherein the subject is an adult subject that presents, before treatment with such compound, a condition characterized by type II diabetes and three or more symptoms selected from the group consisting of: (1) a waist size that is greater than 40 inches if the subject is a male and greater than 35 inches if the subject is a female, (2) a fasting blood glucose level greater than or equal to 110 mg/dL, (3) a fasting triglyceride level of greater than or equal to 150 mg/dL, (4) a high-density lipoprotein (HDL) level of less than 40 mg/dL if the subject is a male and less than 50 mg/dL if the subject is a female, and (5) a blood pressure level of greater than 130/85.

16. The method of claim 1, wherein the subject is a human having a waist measurement to hip measurement ratio that is greater than or about one before treatment with such compound.

17. The method of claim 1, wherein said administering is effective to reduce the waist measurement to hip measurement ratio by at least 2%.

18. A method for reducing visceral fat deposition in a subject, comprising: a) diagnosing a subject as having an excess of visceral fat; and b) administering to said subject a compound that increases the bioactive serum levels of insulin-like growth factor-I (IGF-I) in an amount effective to reduce visceral fat deposition in the subject, wherein the compound is not growth hormone.

19. The method of claim 18, wherein the subject is an adult human that presents, before treatment with such compound, a body composition characterized by a ratio of visceral fat to subcutaneous fat that is higher than the ratio of visceral fat to subcutaneous fat that characterizes the average body composition of normal adult humans of the same body mass index (BMI) and gender as the subject.

20. The method of claim 18, wherein either (i) the subject is an adult human male and is type II diabetic and has a waist size of at least 40 inches before treatment with such compound or (ii) the subject is an adult human female and is type II diabetic and has a waist size of at least 35 inches before treatment with such compound.

21. The method of claim 20, wherein the compound is IGF-I.

22. A method of ameliorating visceral fat deposition caused by a medicament, comprising: a) diagnosing a subject as having an excess of visceral fat; and b) administering to said subject a medicament of interest and a compound that increases the bioactive serum levels of insulin-like growth factor-I (IGF-I), said compound being administered in an amount effective to ameliorate visceral fat deposition caused by administration of the medicament, and wherein the compound is not growth hormone.

\* \* \* \* \*